United States Patent
Kim et al.

(10) Patent No.: US 10,456,347 B2
(45) Date of Patent: Oct. 29, 2019

(54) COMPOSITION FOR INJECTION OF HYALURONIC ACID, CONTAINING HYALURONIC ACID DERIVATIVE AND DNA FRACTION, AND USE THEREOF

(71) Applicant: BMI KOREA CO., LTD, Jeju-si (KR)

(72) Inventors: Min-Kyoung Kim, Jeju-si (KR); Koo Woo, Jeju-si (KR); Yeong Jun Baik, Seoul (KR); Sung Hee Lee, Seongnam-si (KR); Kyeong Woo Min, Asan-si (KR)

(73) Assignee: BMI KOREA CO., LTD, Jeju-si (KR)

( * ) Notice: Subject to any disclaimer, the term of this patent is extended or adjusted under 35 U.S.C. 154(b) by 0 days.

(21) Appl. No.: 15/775,855

(22) PCT Filed: Nov. 24, 2016

(86) PCT No.: PCT/KR2016/013652
§ 371 (c)(1),
(2) Date: May 14, 2018

(87) PCT Pub. No.: WO2017/091017
PCT Pub. Date: Jun. 1, 2017

(65) Prior Publication Data
US 2018/0325798 A1 Nov. 15, 2018

(30) Foreign Application Priority Data
Nov. 24, 2015 (KR) .................. 10-2015-0164932

(51) Int. Cl.
| | | |
|---|---|---|
| *A61K 8/73* | (2006.01) | |
| *A61K 31/728* | (2006.01) | |
| *A61Q 19/08* | (2006.01) | |
| *C08B 37/08* | (2006.01) | |
| *C08J 3/24* | (2006.01) | |
| *A61K 8/96* | (2006.01) | |
| *A61K 8/04* | (2006.01) | |
| *A61L 31/00* | (2006.01) | |
| *C08L 5/08* | (2006.01) | |
| *A61K 9/00* | (2006.01) | |

(52) U.S. Cl.
CPC .............. *A61K 8/735* (2013.01); *A61K 8/042* (2013.01); *A61K 8/96* (2013.01); *A61K 31/728* (2013.01); *A61L 31/00* (2013.01); *A61Q 19/08* (2013.01); *C08B 37/0072* (2013.01); *C08J 3/24* (2013.01); *C08J 3/248* (2013.01); *C08L 5/08* (2013.01); *A61K 9/0021* (2013.01); *A61K 2800/91* (2013.01); *C08J 3/242* (2013.01); *C08J 2305/08* (2013.01)

(58) Field of Classification Search
CPC ............ A61K 8/735; A61K 8/042; A61K 8/96
See application file for complete search history.

(56) References Cited

U.S. PATENT DOCUMENTS

| 9,339,450 B2 | 5/2016 | Thorel |
| 2003/0148995 A1 | 8/2003 | Piron et al. |
| 2014/0080897 A1* | 3/2014 | Hahn .................. A61K 31/713 514/44 A |

FOREIGN PATENT DOCUMENTS

| EP | 2407147 | 1/2012 |
| JP | 2002-510610 | 4/2002 |
| JP | 2005-176830 | 7/2005 |
| JP | 2005-272398 | 10/2005 |
| JP | 2011-529762 | 12/2011 |
| KR | 10-1476381 | 8/2010 |
| KR | 10-2011-0040966 | 4/2011 |
| KR | 10-2012-0089433 | 8/2012 |
| KR | 10-2014-0037449 | 3/2014 |
| KR | 10-2014-0101018 | 8/2014 |
| KR | 10-2015-0029578 | 3/2015 |
| KR | 10-2015-0064090 | 6/2015 |
| KR | 10-1710639 | 3/2017 |
| RU | 2013108857 | 9/2014 |
| WO | 1994-025078 | 11/1994 |
| WO | 2013-021249 | 2/2013 |
| WO | 2014-198406 | 12/2014 |
| WO | 2015/125117 | 8/2015 |

OTHER PUBLICATIONS

The Russian Federal Service for Intellectual Property (ROSPATENT), A Patent Search Report of RU 2018120710 dated Apr. 3, 2019.
EPO, extended European Search Report of the corresponding European Patent Application No. 16868913.1.dated Jul. 15, 2019.

* cited by examiner

*Primary Examiner* — Pancham Bakshi
(74) *Attorney, Agent, or Firm* — Lex IP Meister, PLLC

(57) ABSTRACT

The present invention refers to the injectable hyaluronic acid composition which is crosslinked viscoelastic hyaluronic acid gel comprising DNA fractions. More particularly, it refers to the injectable hyaluronic acid composition comprising a hyaluronic acid composition crosslinked in the basic conditions with the degree of crosslinking between 0.1 and 200%, which is mixed with the DNA fractions of 0.1 to 50 wt %. The DNA fractions are selected, for example, from polynucleotide (PN) and polydeoxyribonucleotide (PDRN). The composition used for cosmetic purposes or therapeutic purposes, have improved viscoelastic rheological properties and enzyme resistance.

12 Claims, 26 Drawing Sheets

[Fig. 1a]
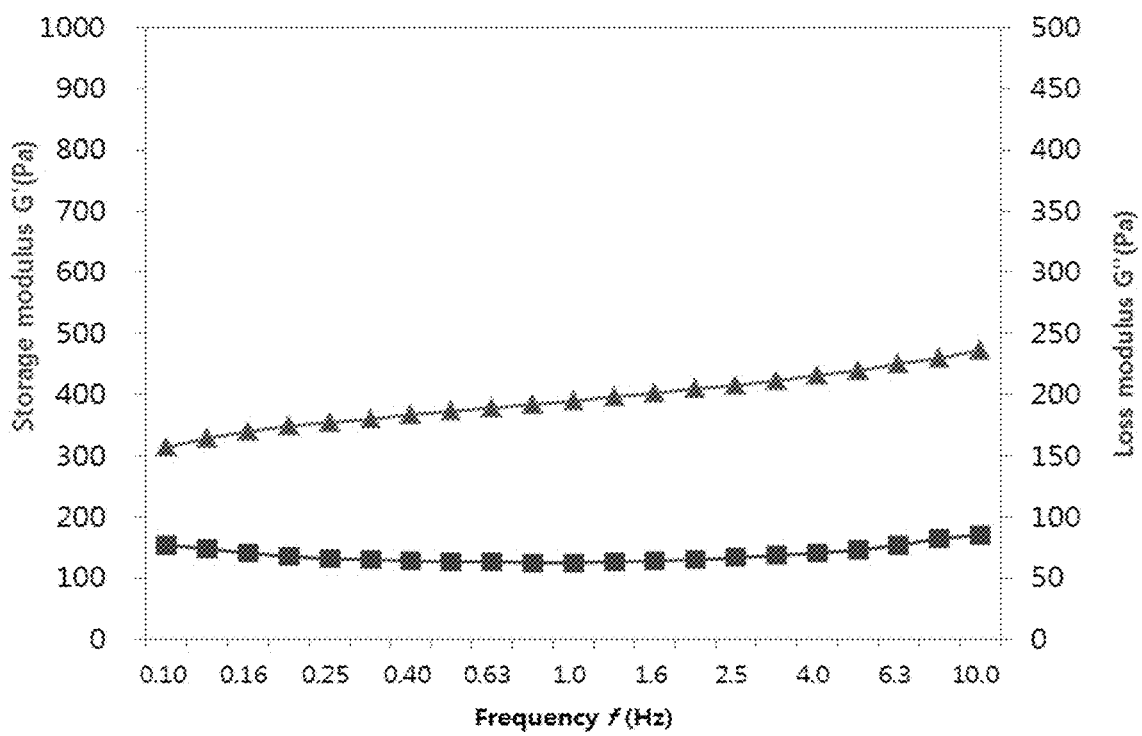
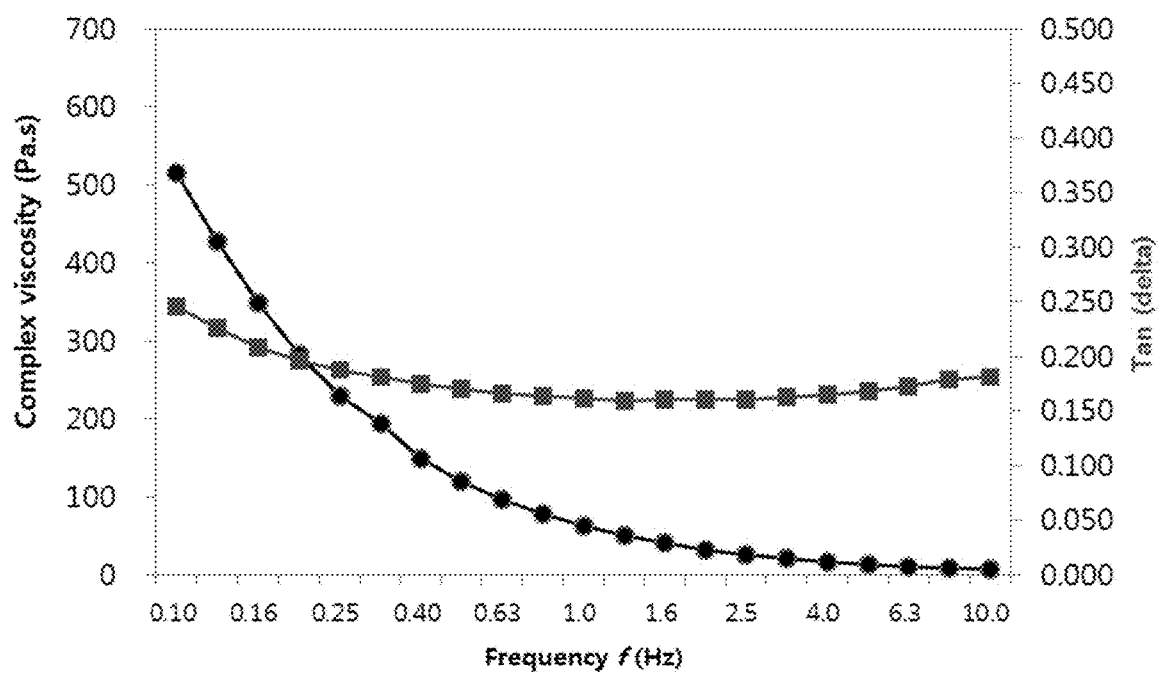

[Fig. 1b]
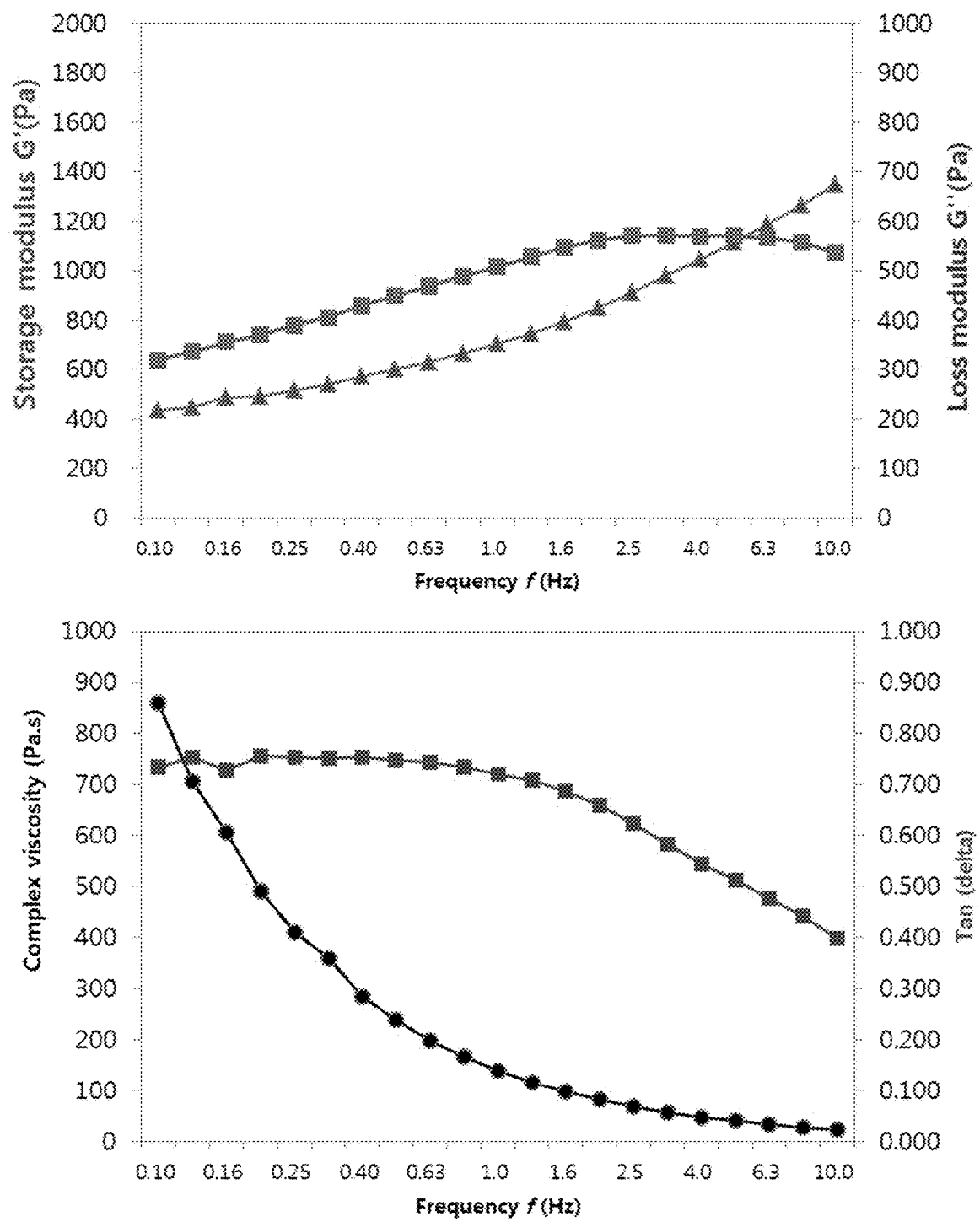

[Fig. 1c]
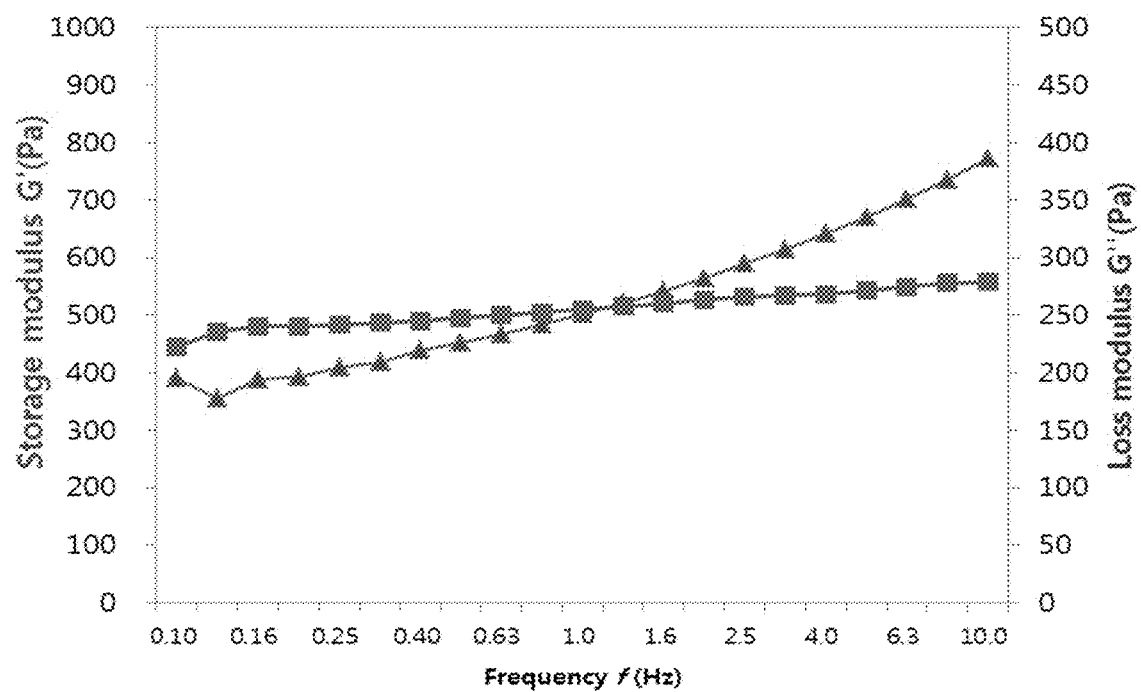
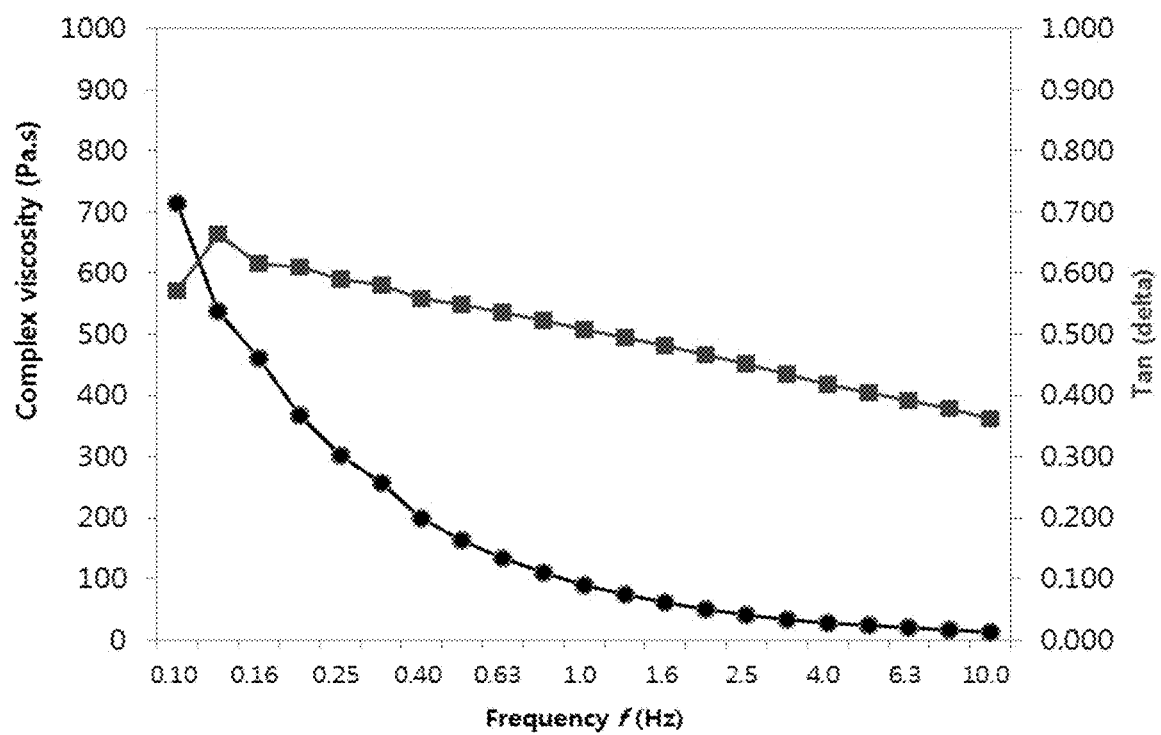

[Fig. 1d]
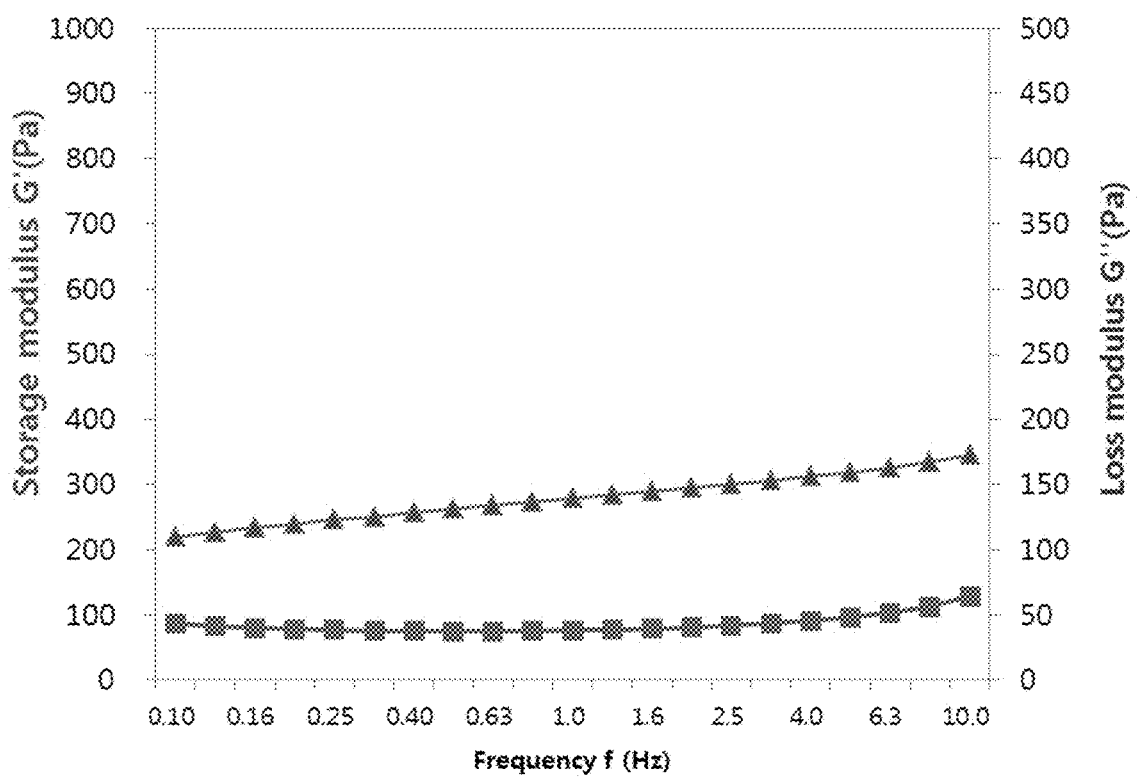
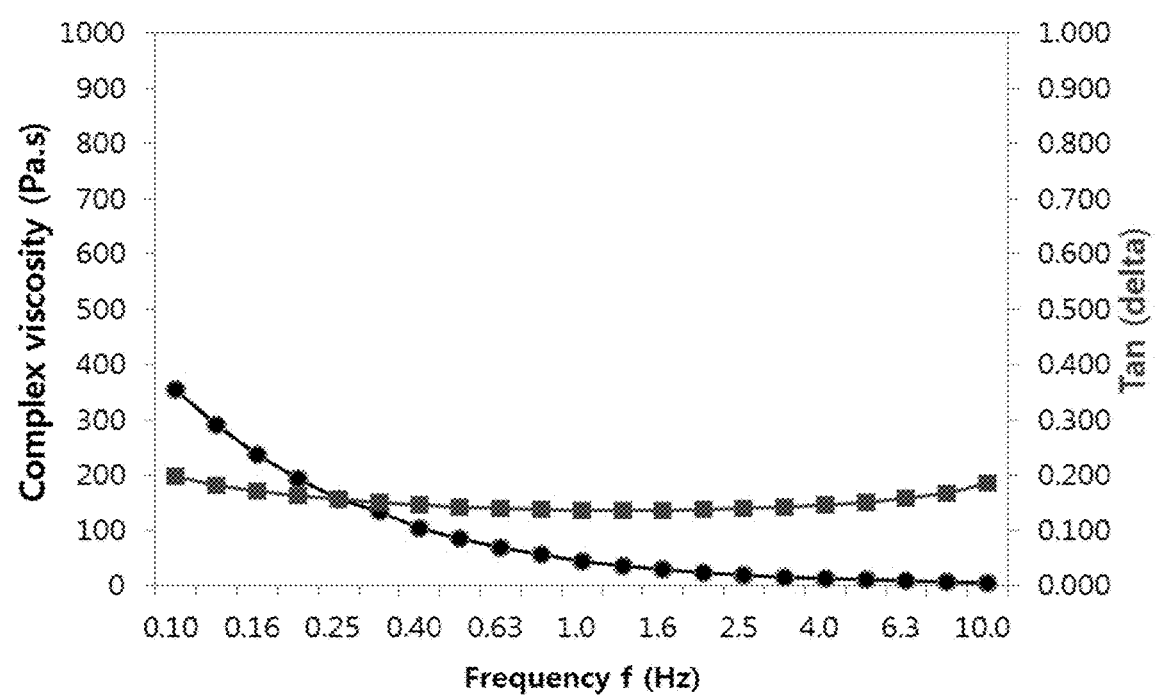

[Fig. 1e]
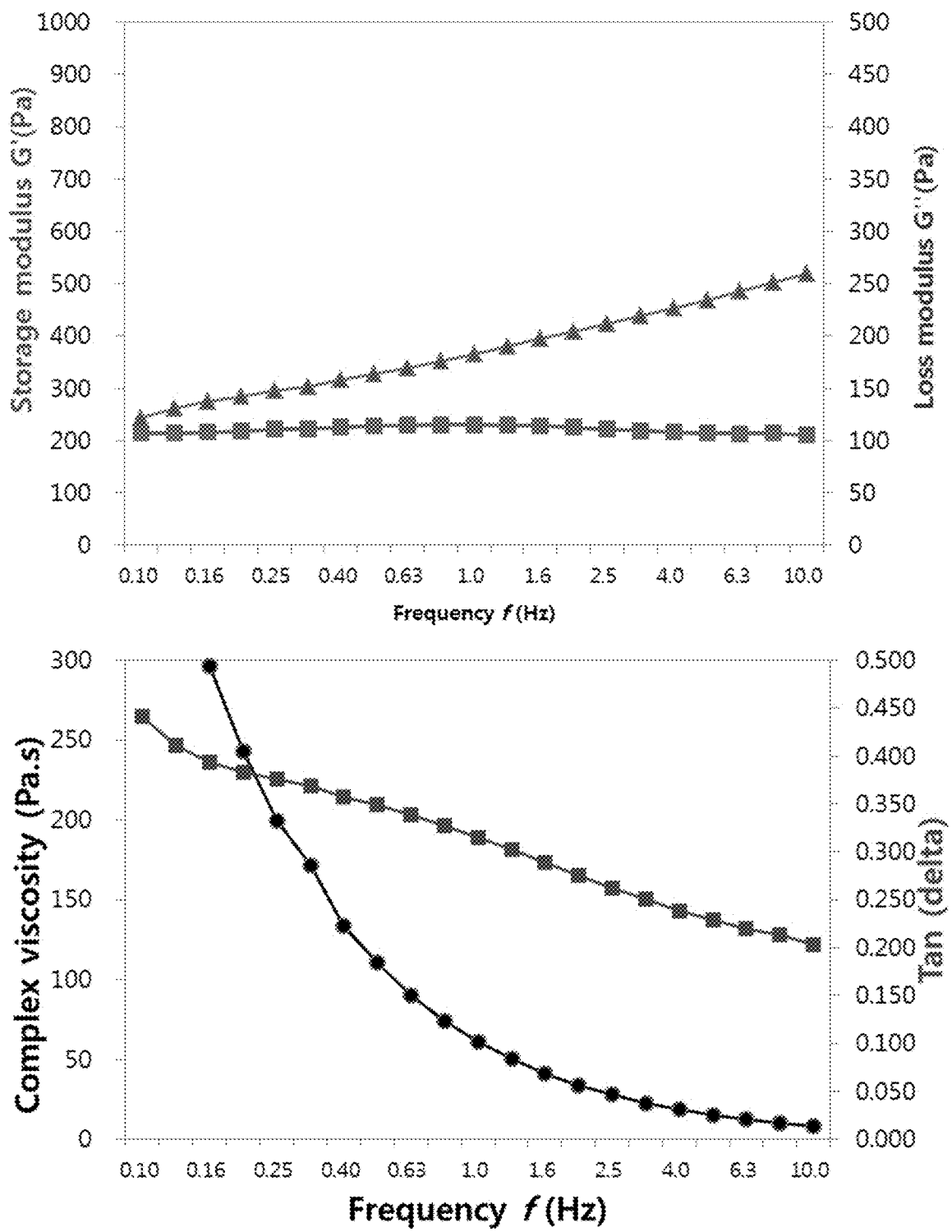

[Fig. 1f]
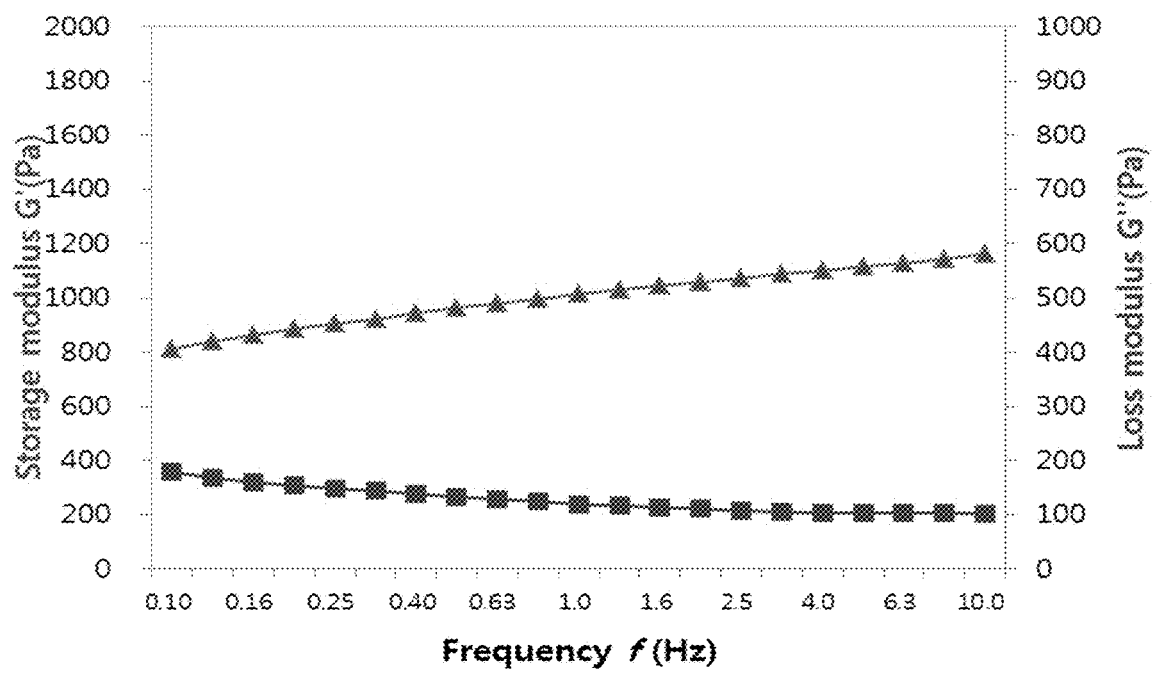
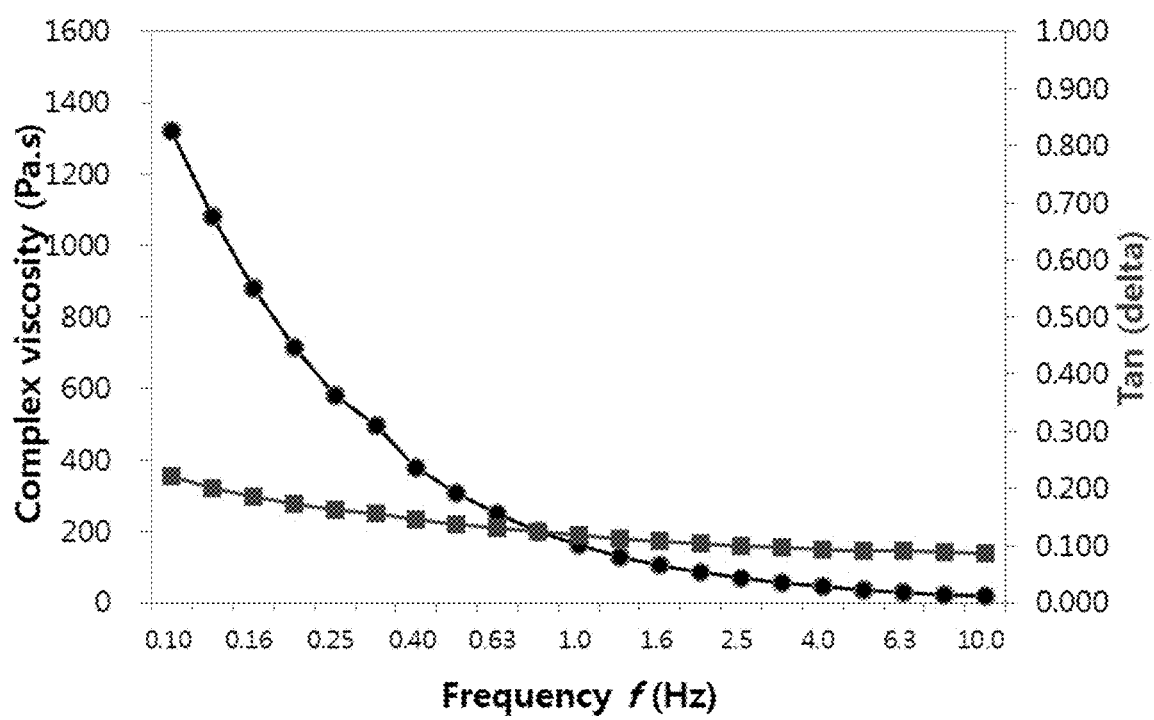

[Fig. 1g]
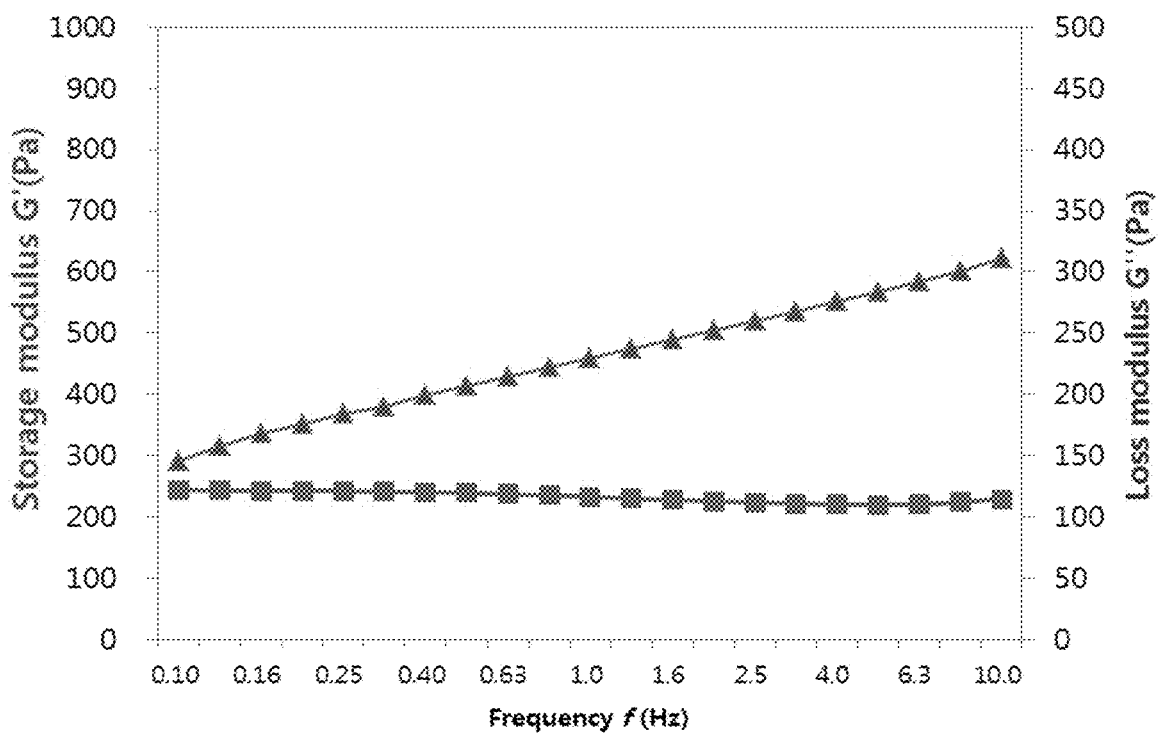
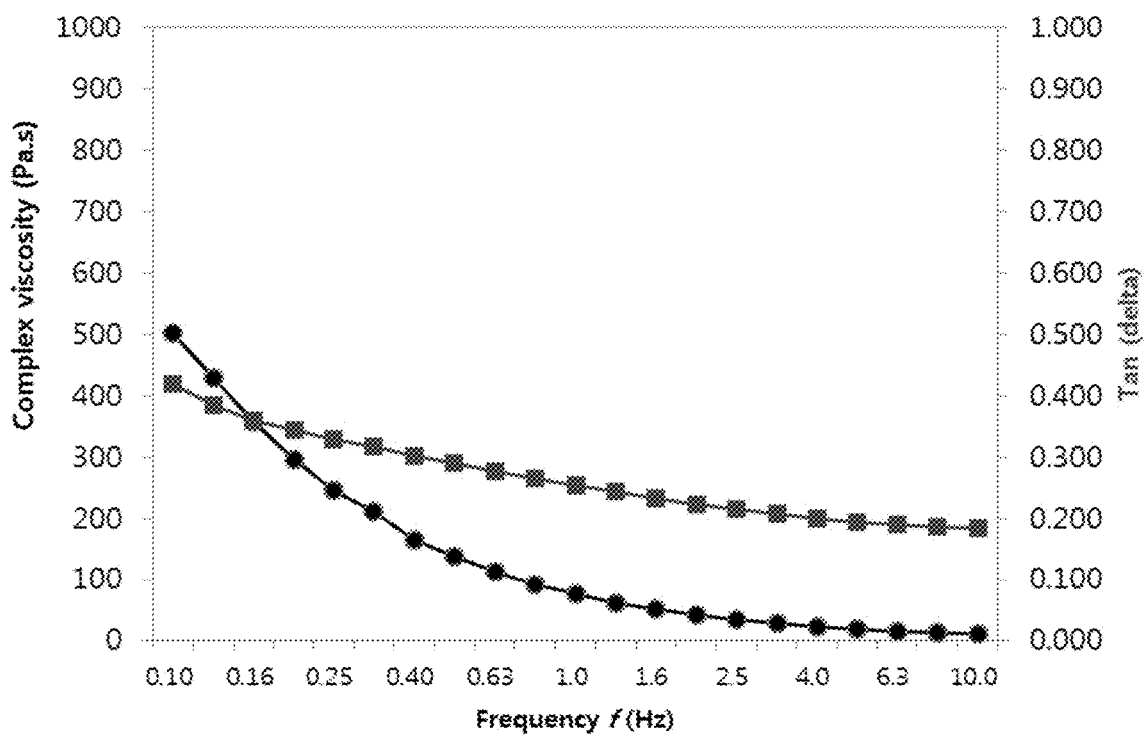

[Fig. 1h]
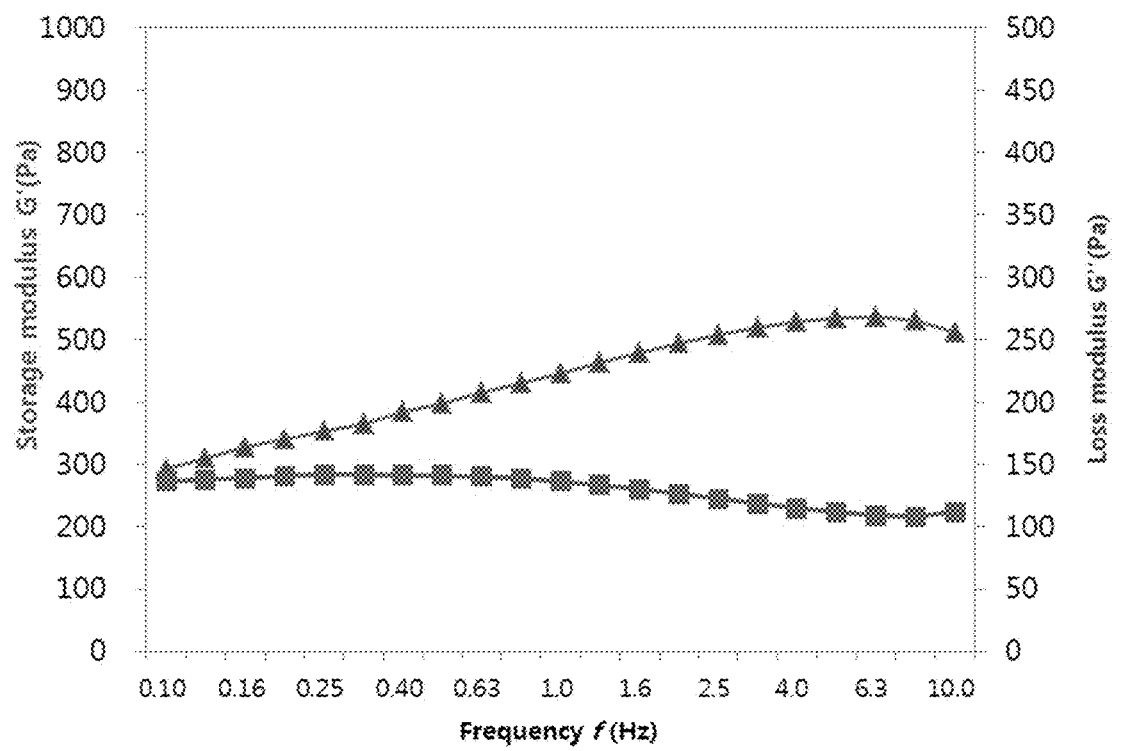
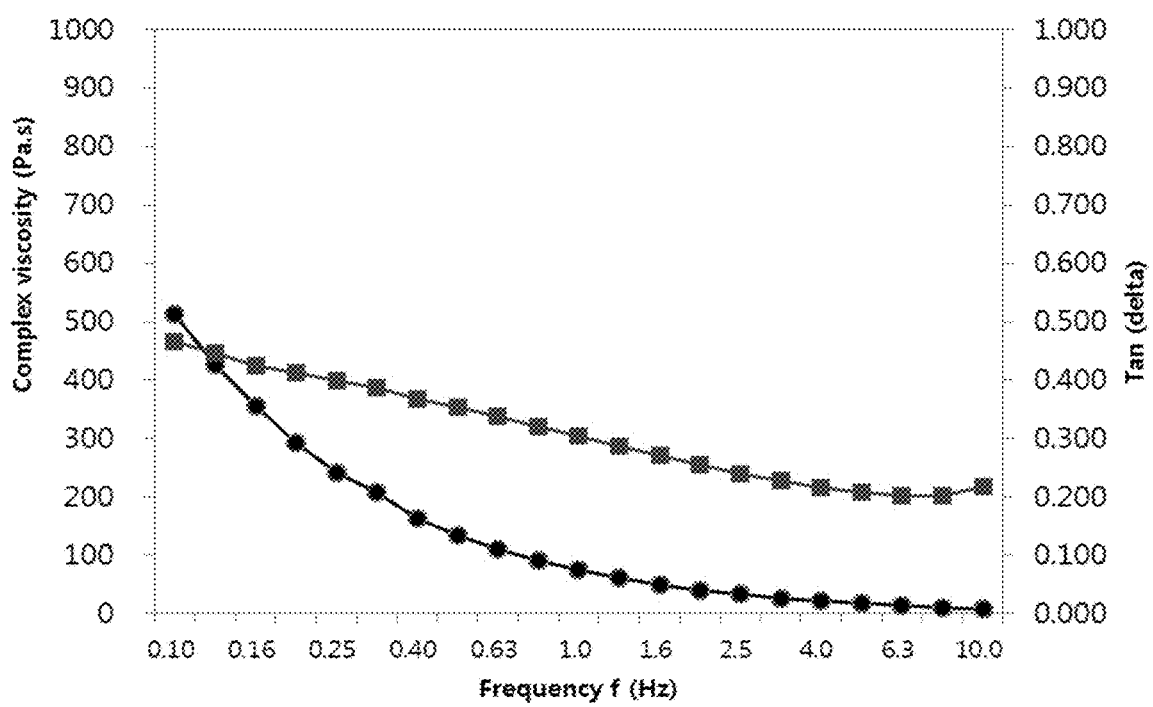

[Fig. 1i]
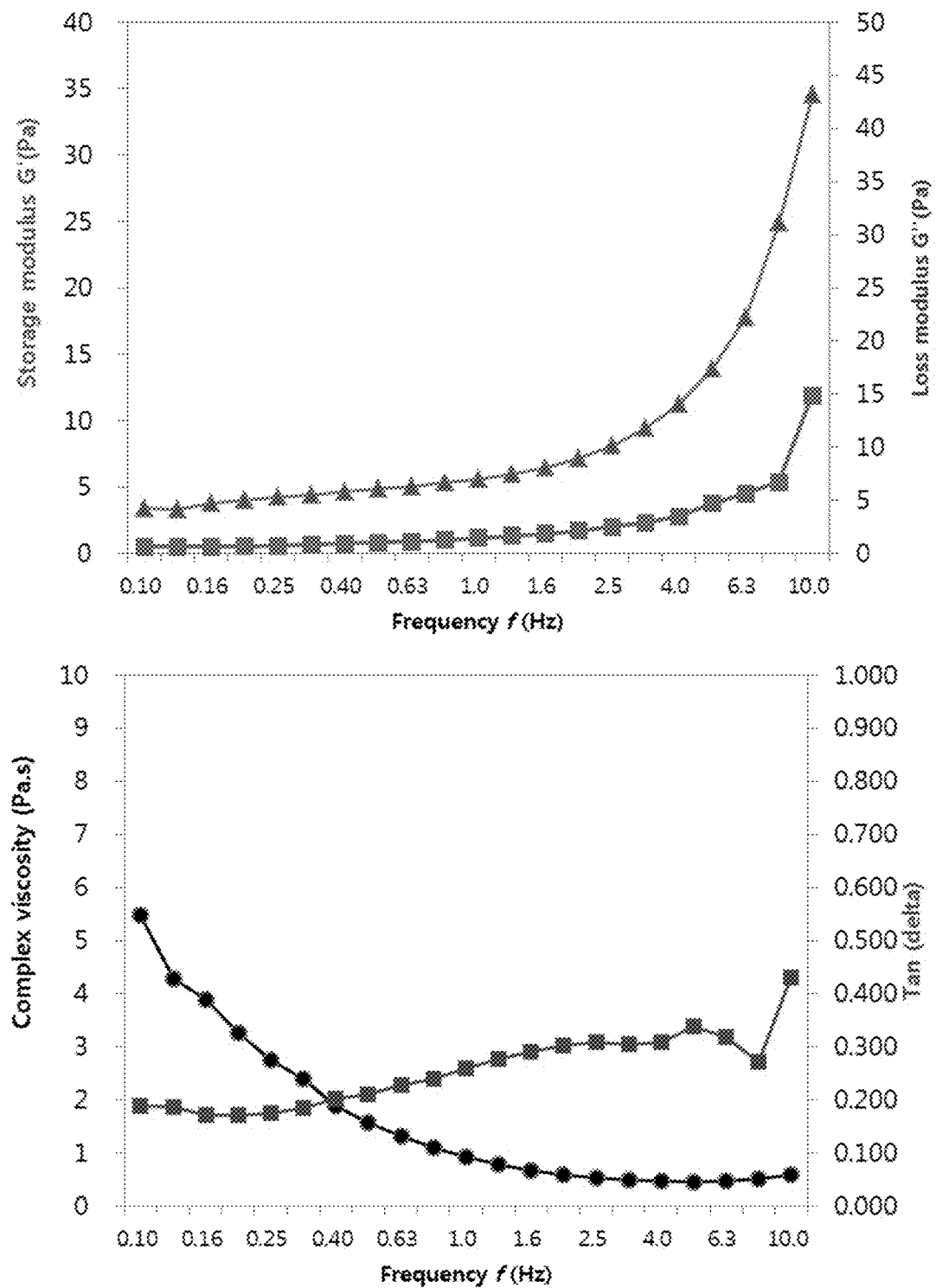

[Fig. 2a]
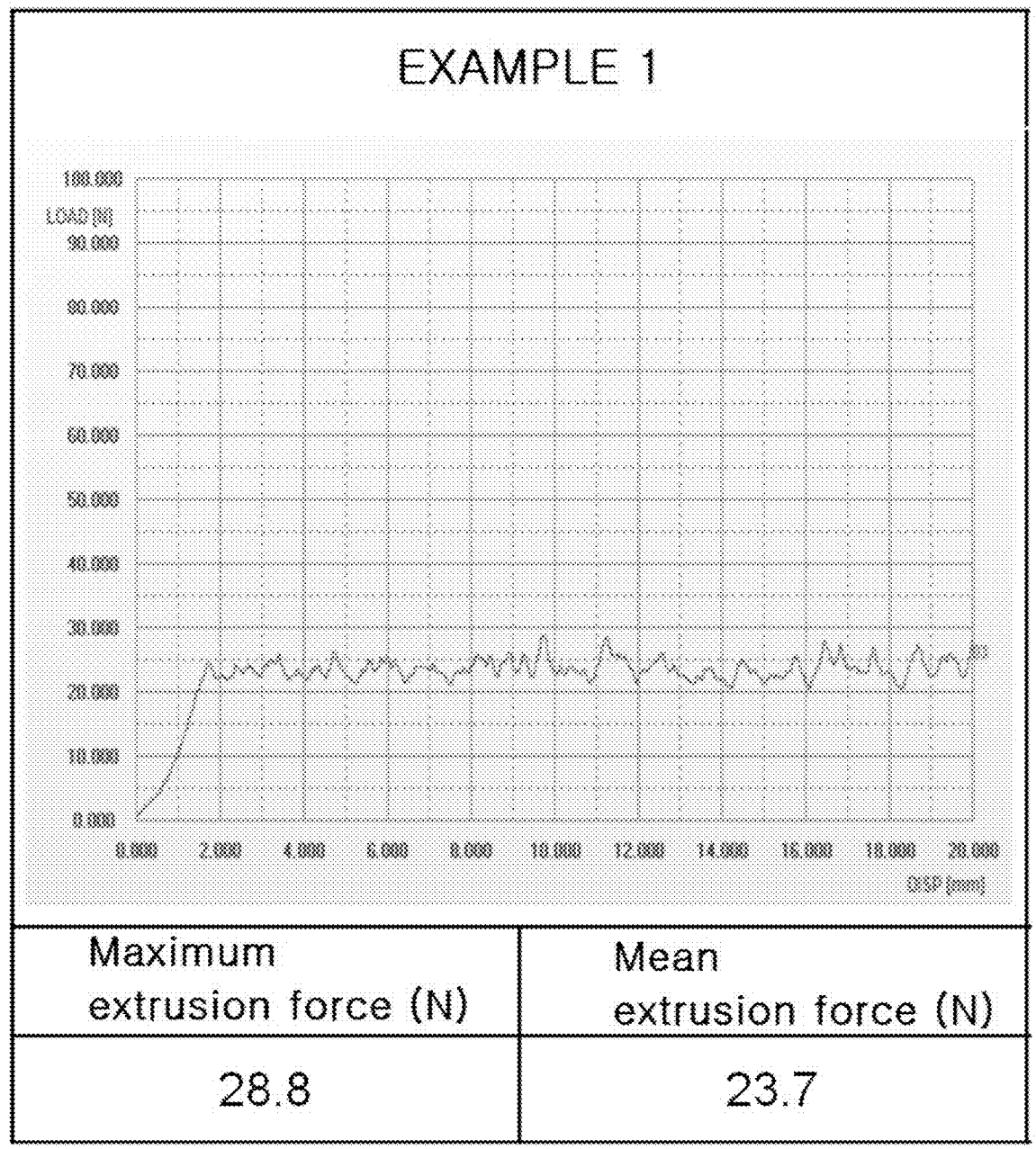

[Fig. 2b]
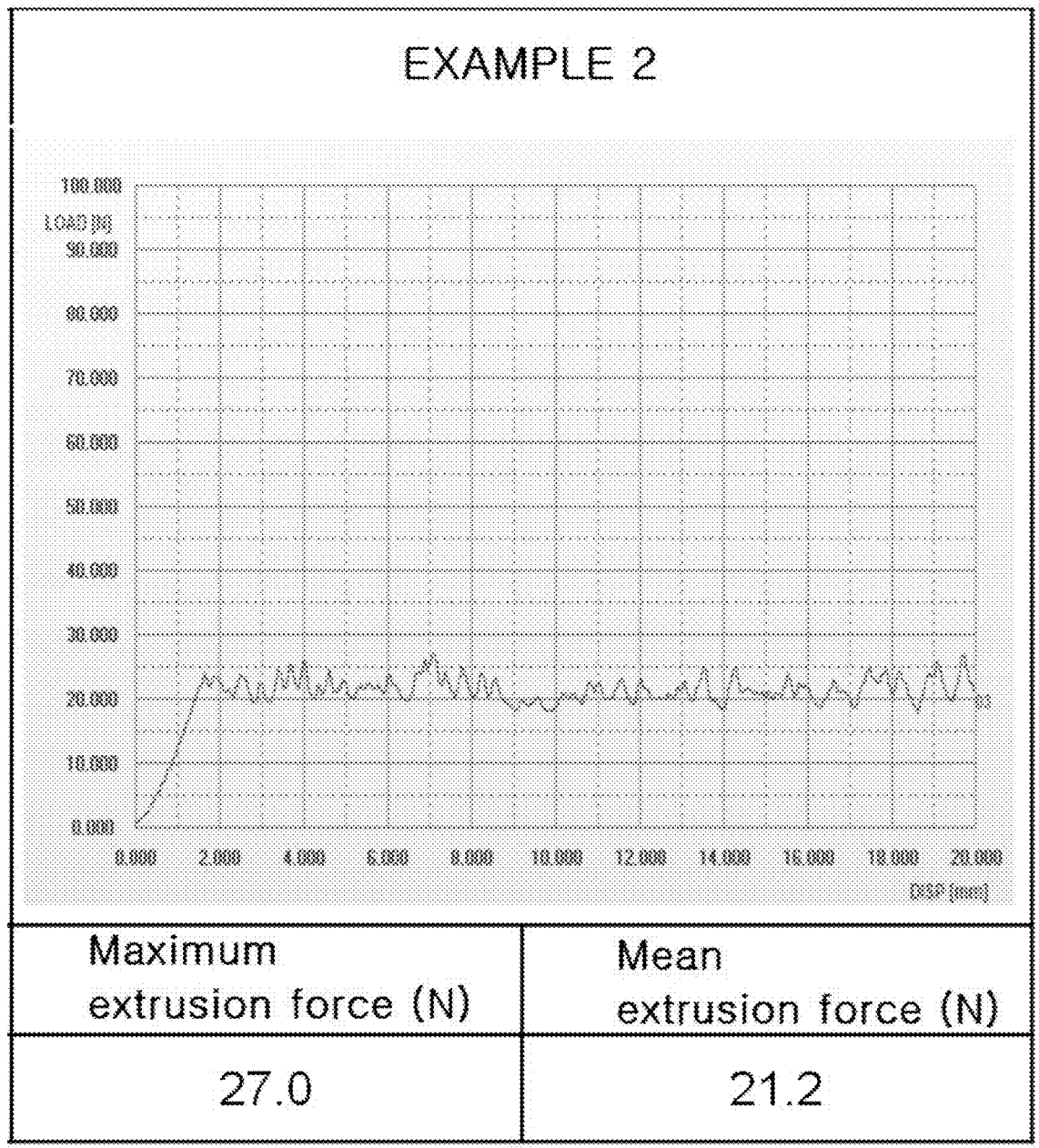

[Fig. 3]
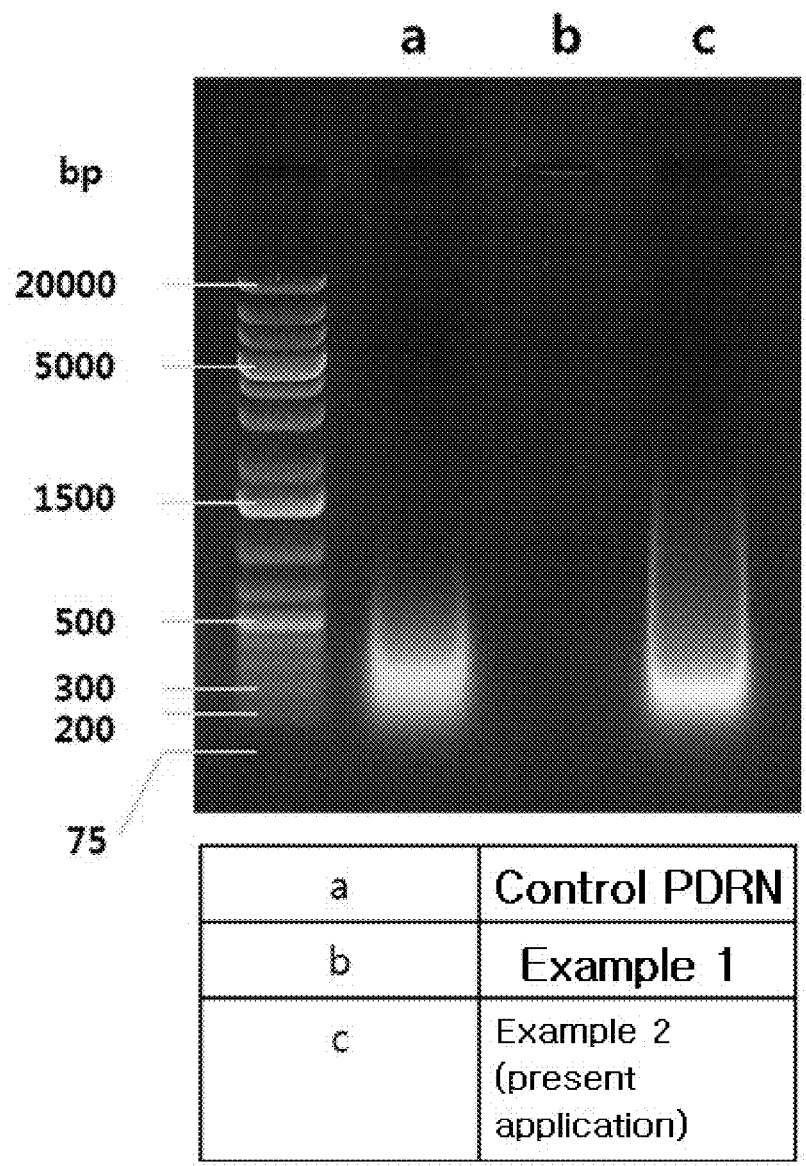

[Fig. 4a]
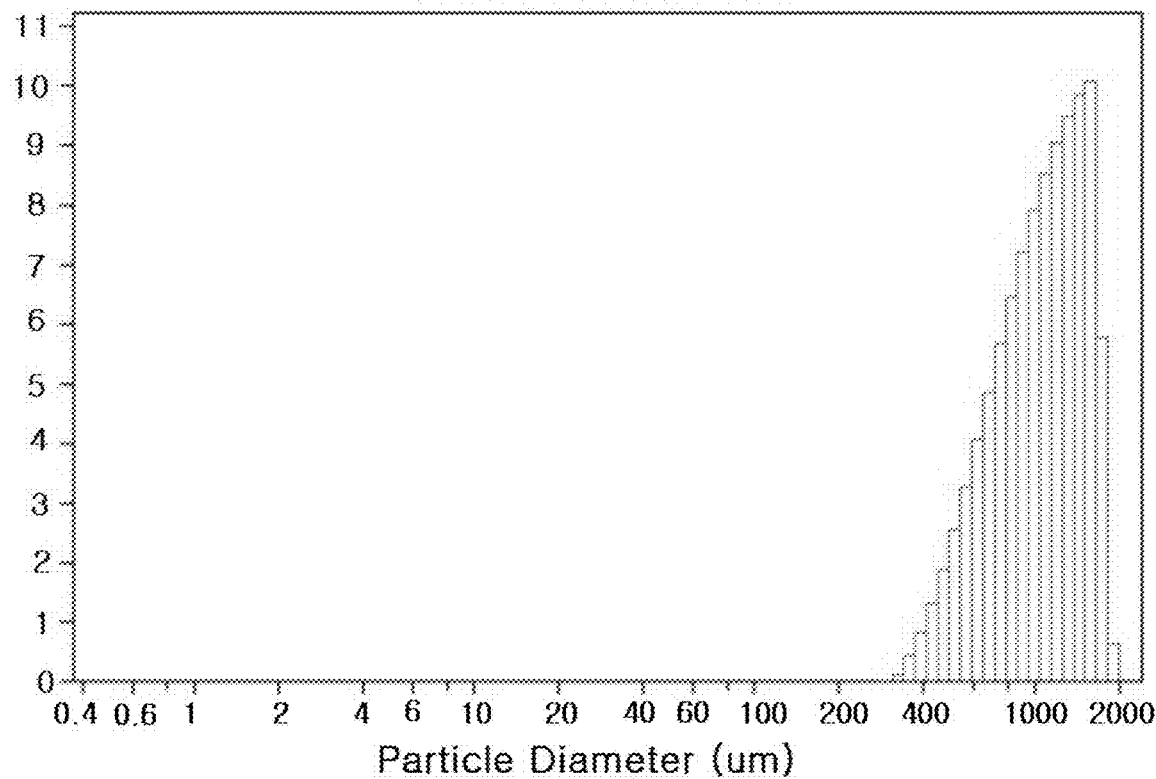

[Fig. 4b]
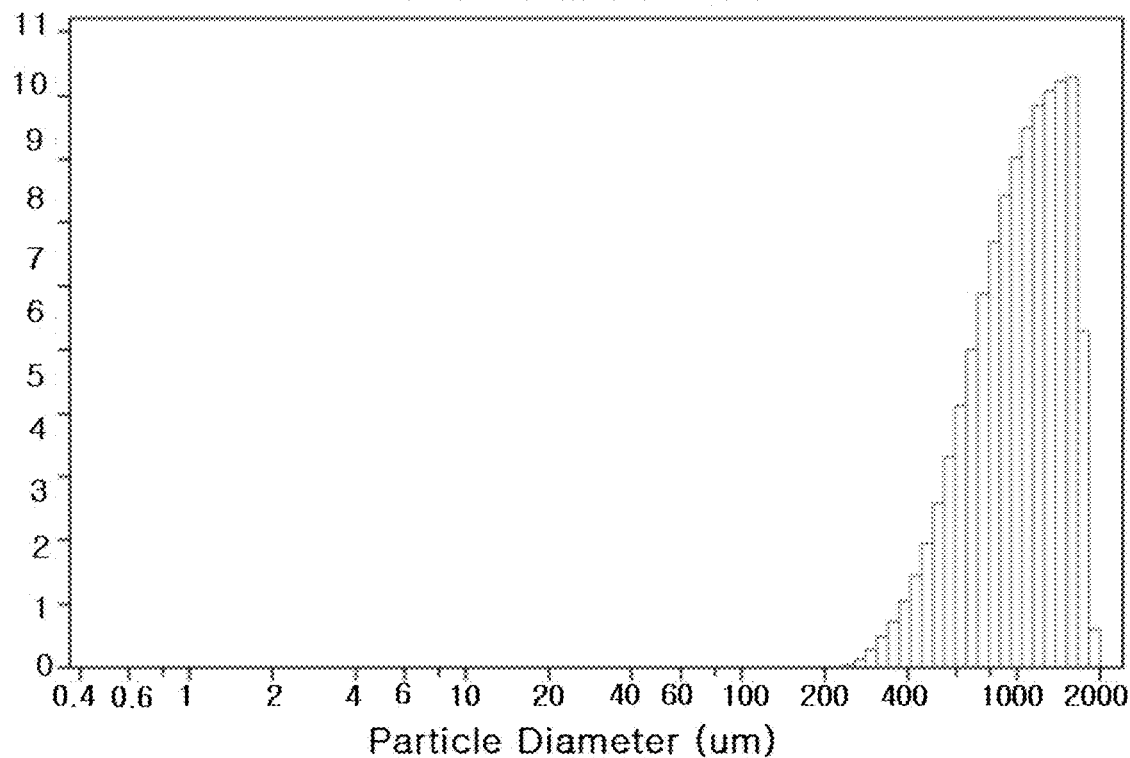

[Fig. 4c]
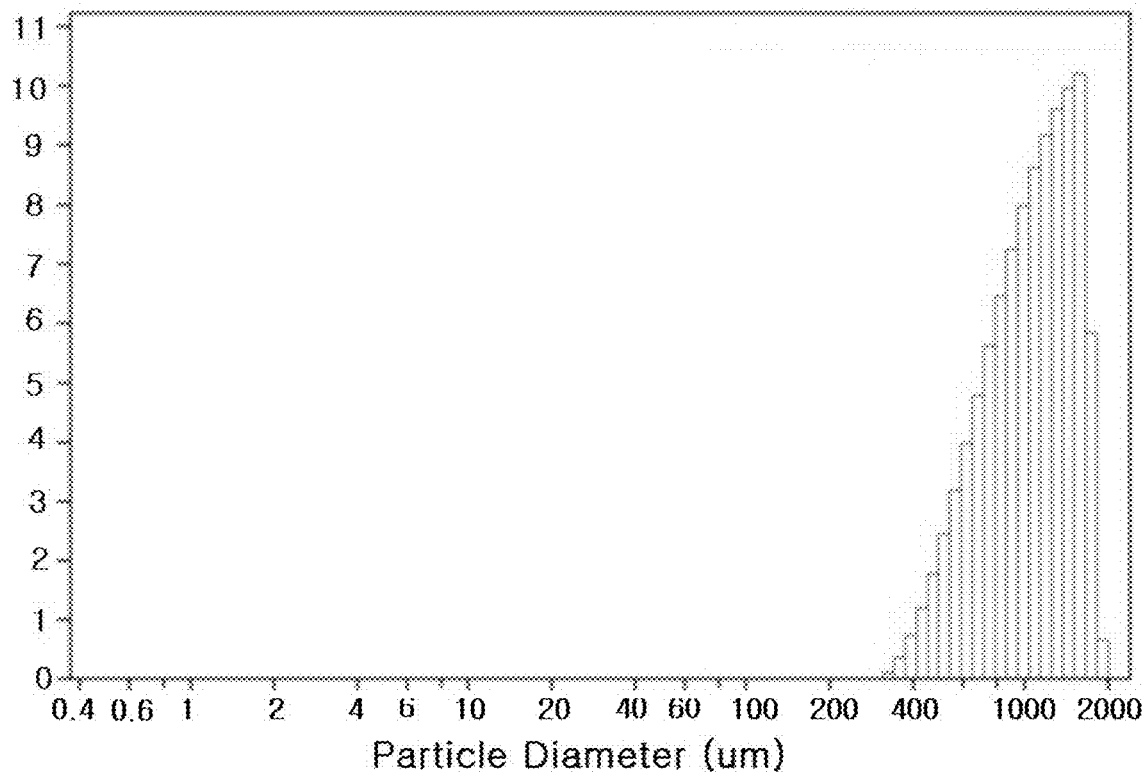

[Fig. 4d]
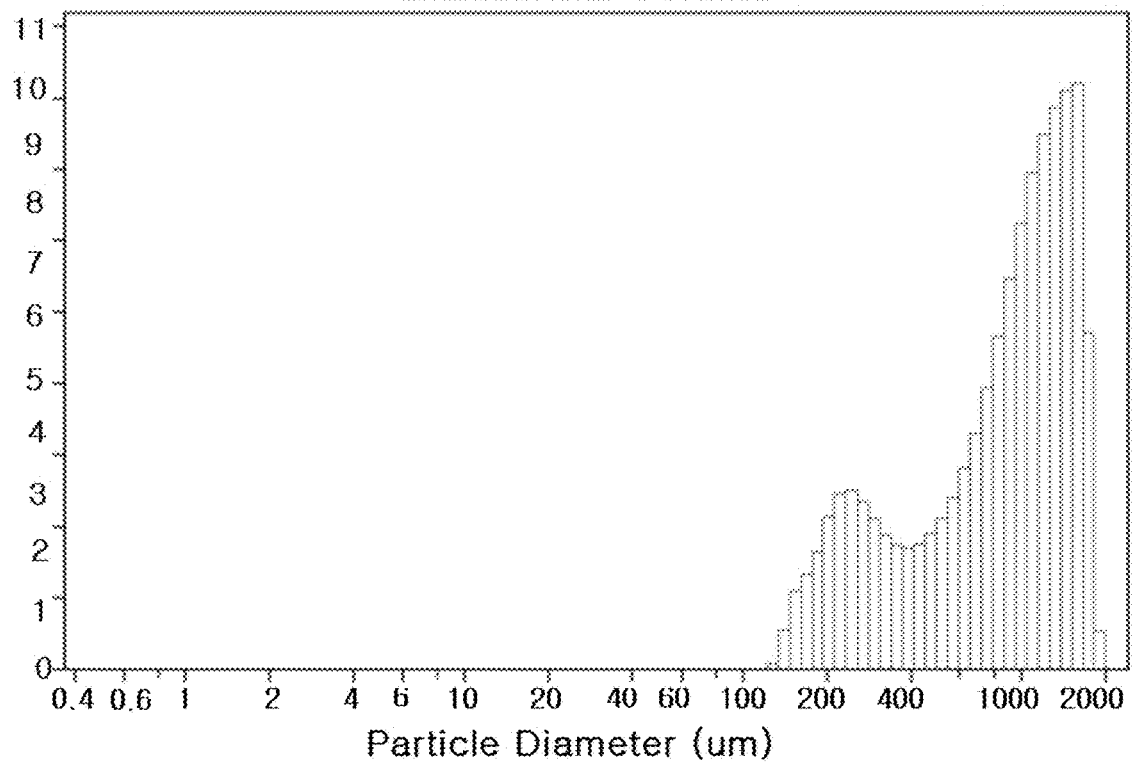

[Fig. 5]
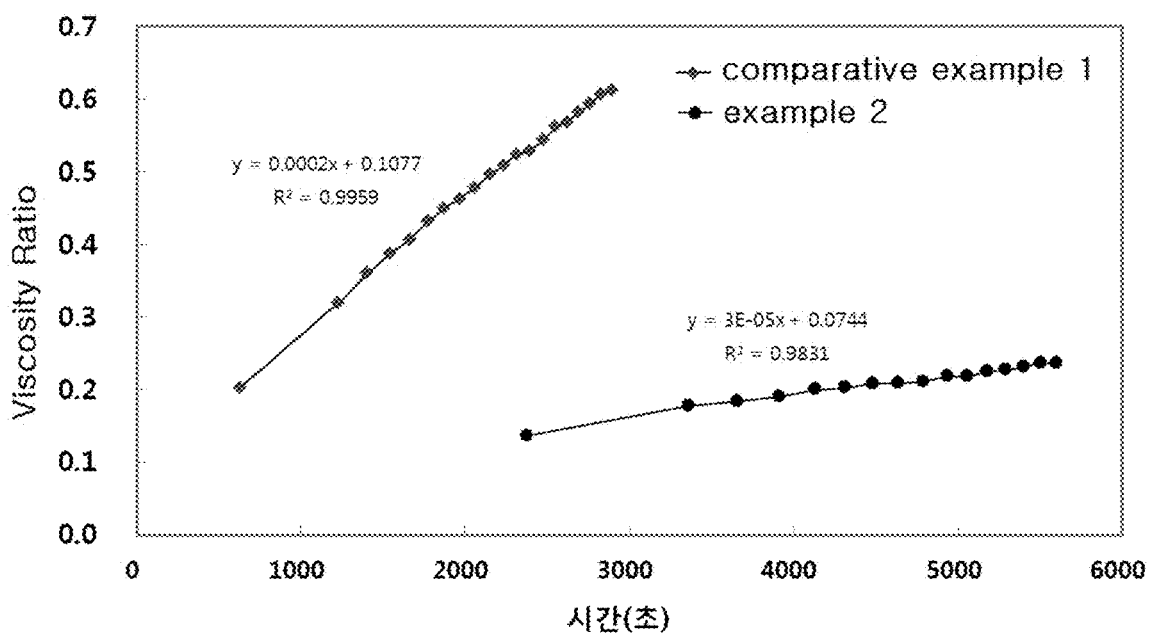

[Fig. 6a]
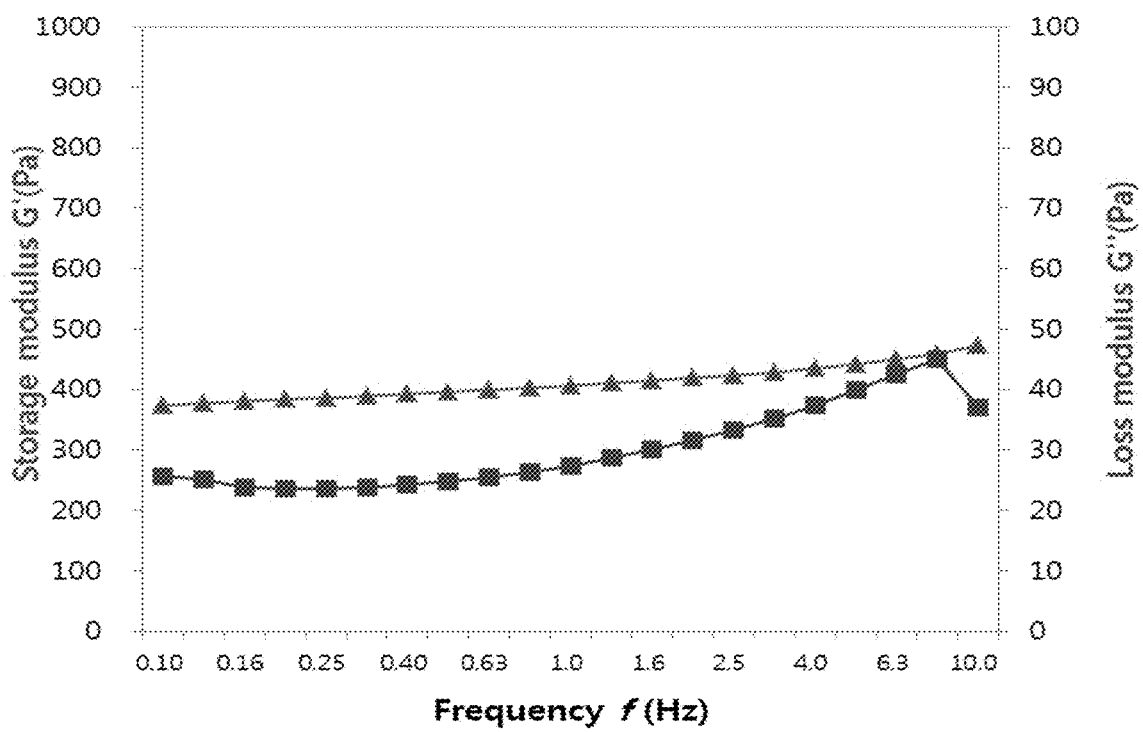
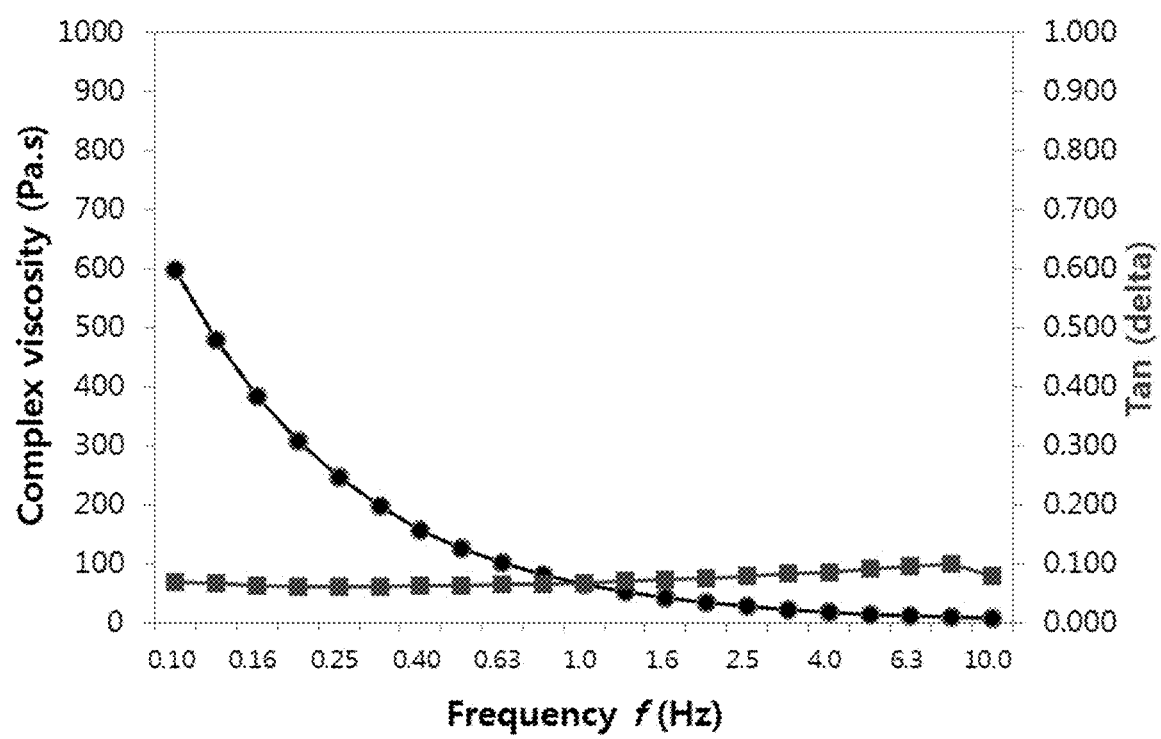

[Fig. 6b]
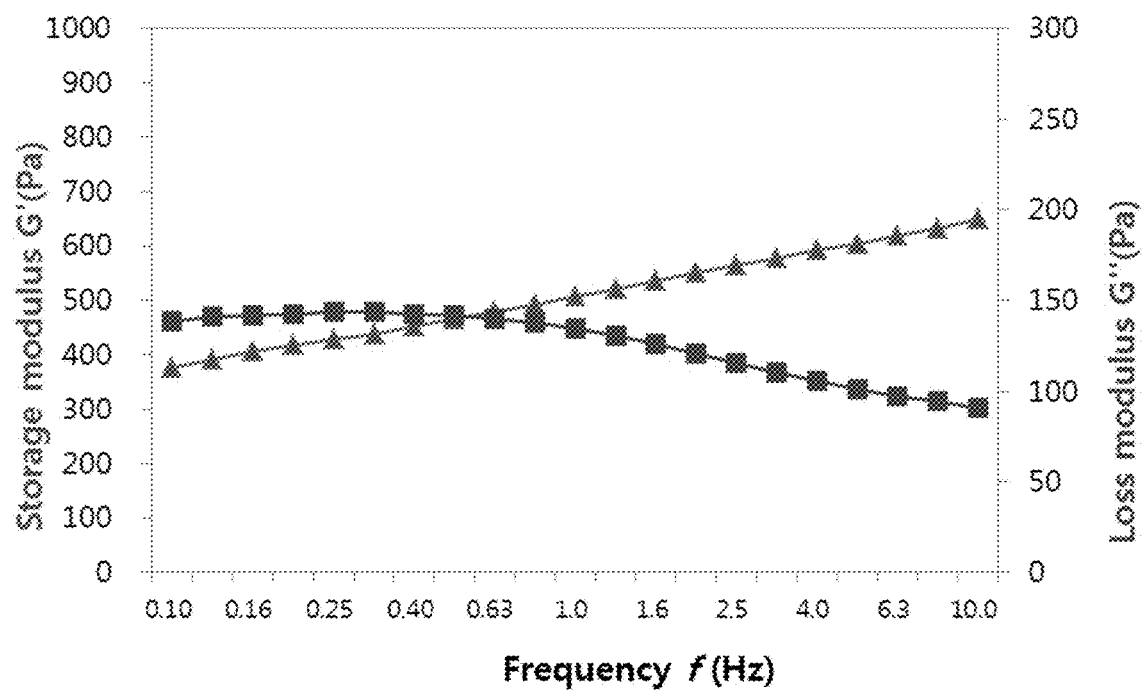
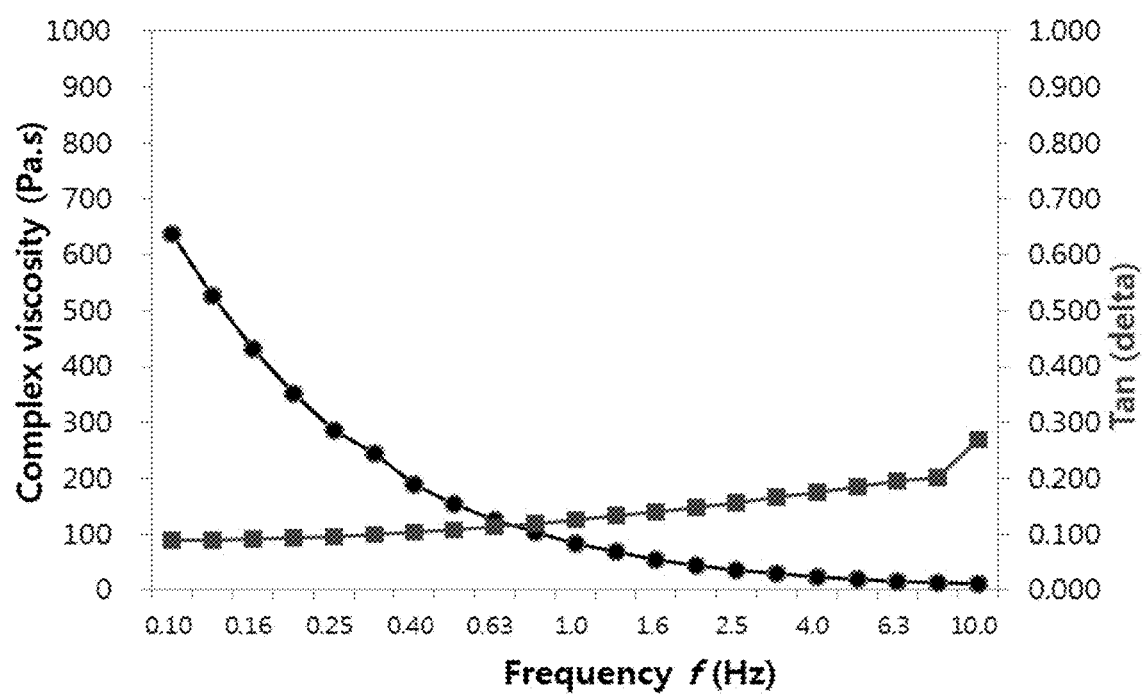

[Fig. 6c]
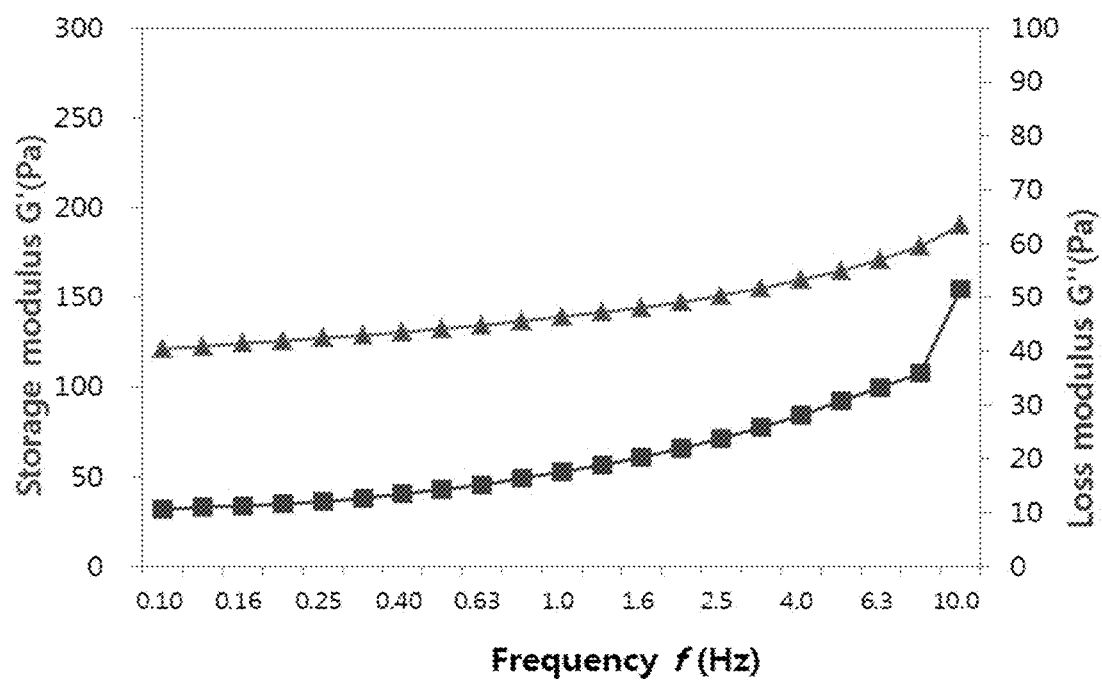
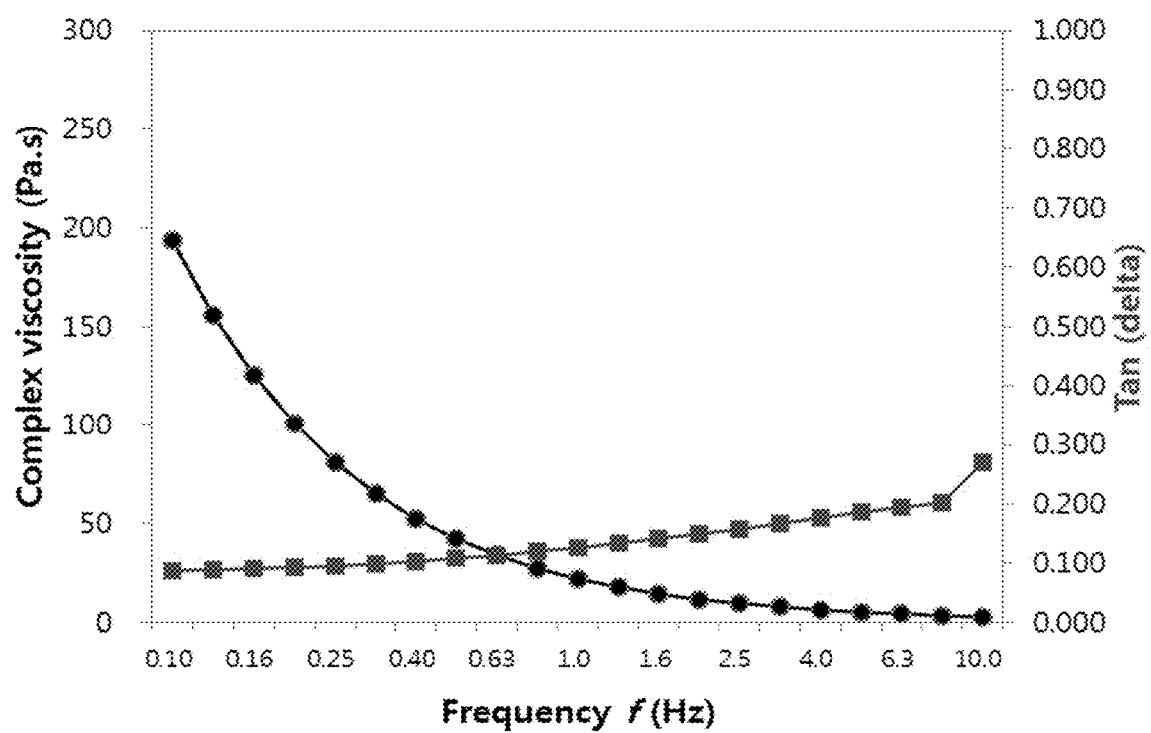

[Fig. 6d]
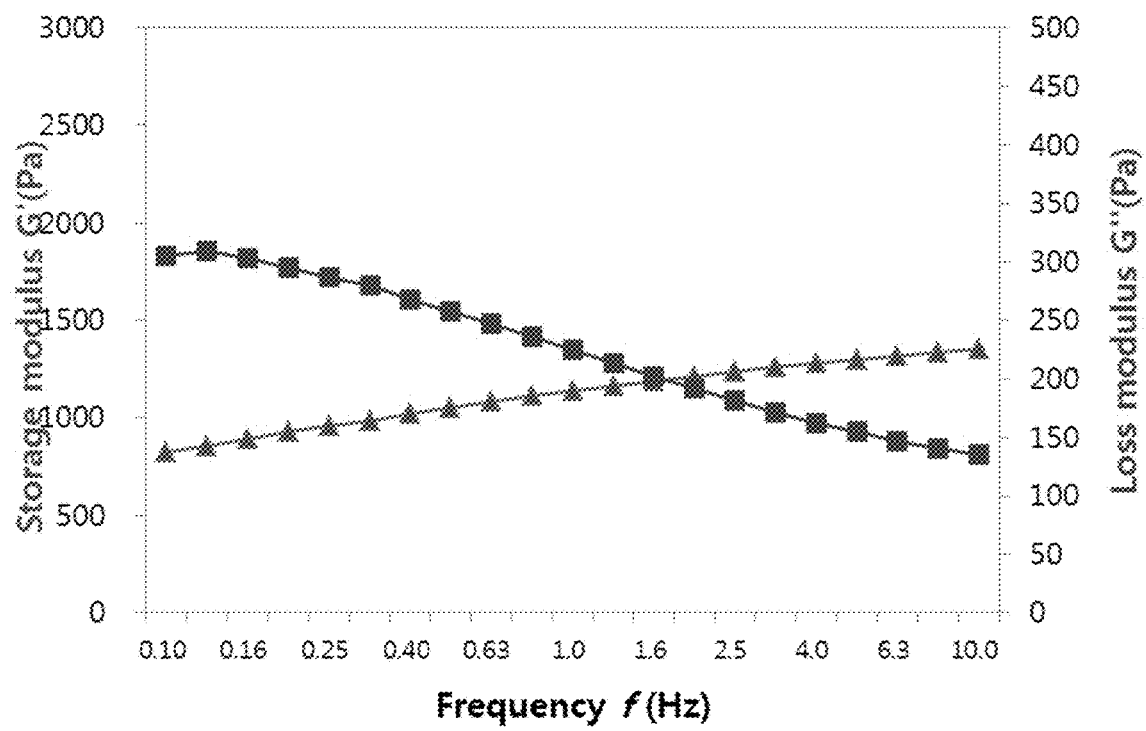
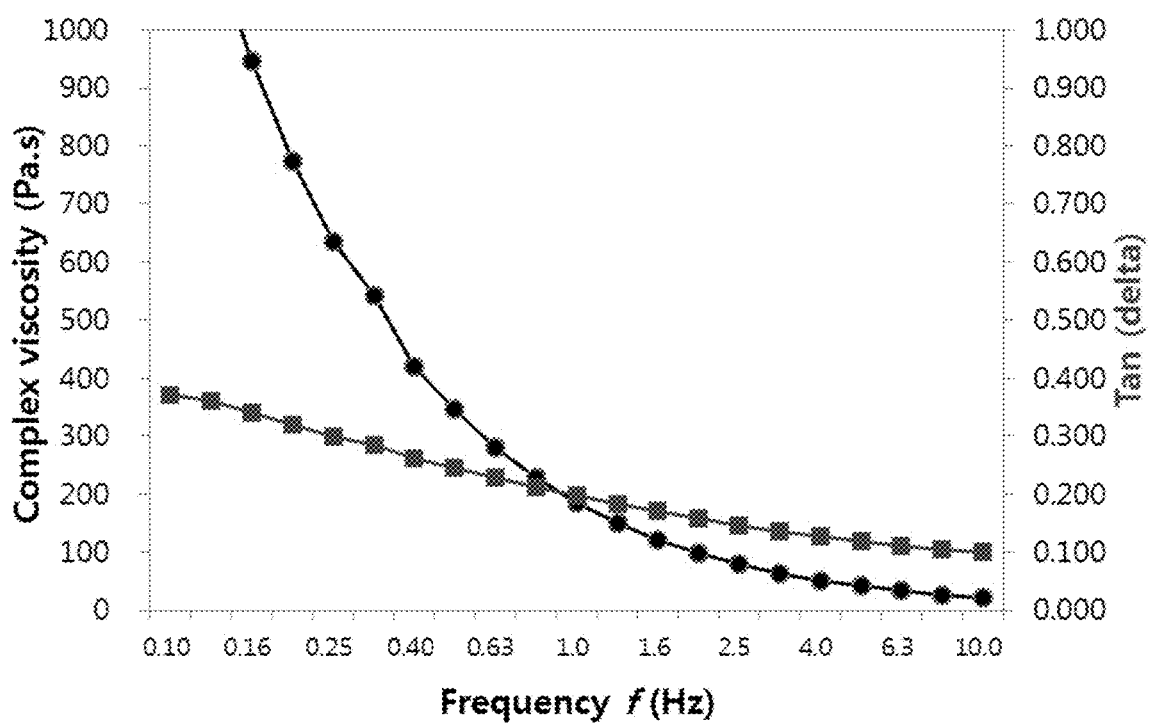

[Fig. 6e]
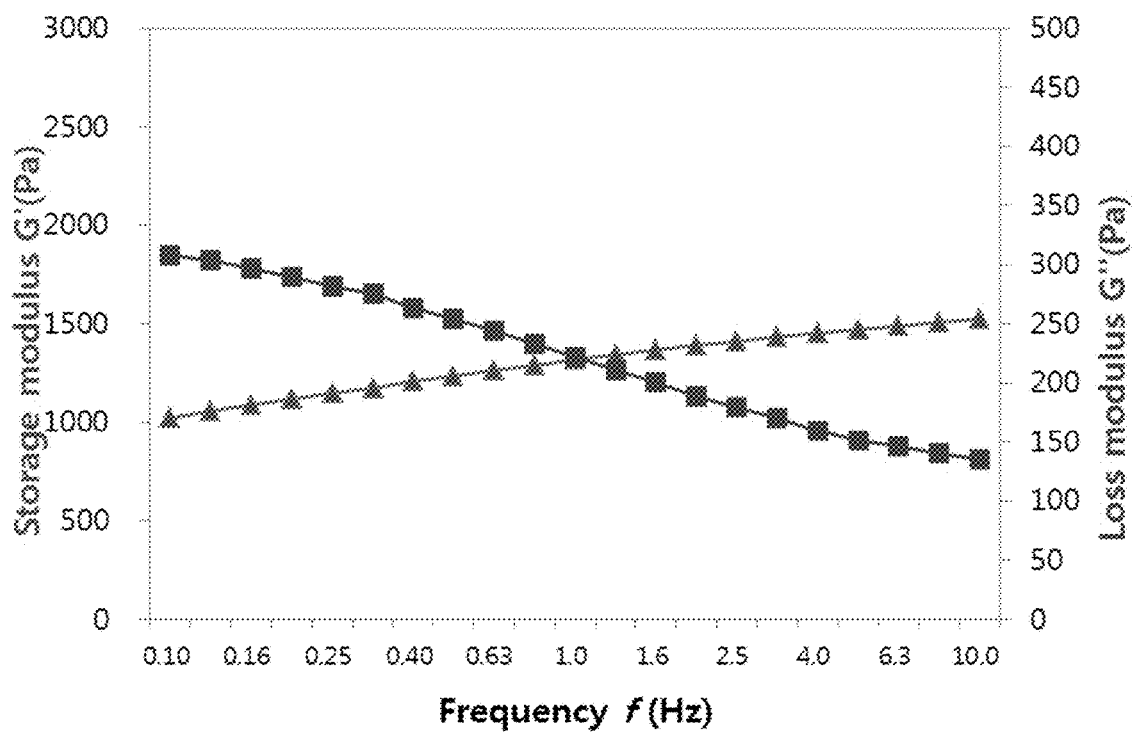
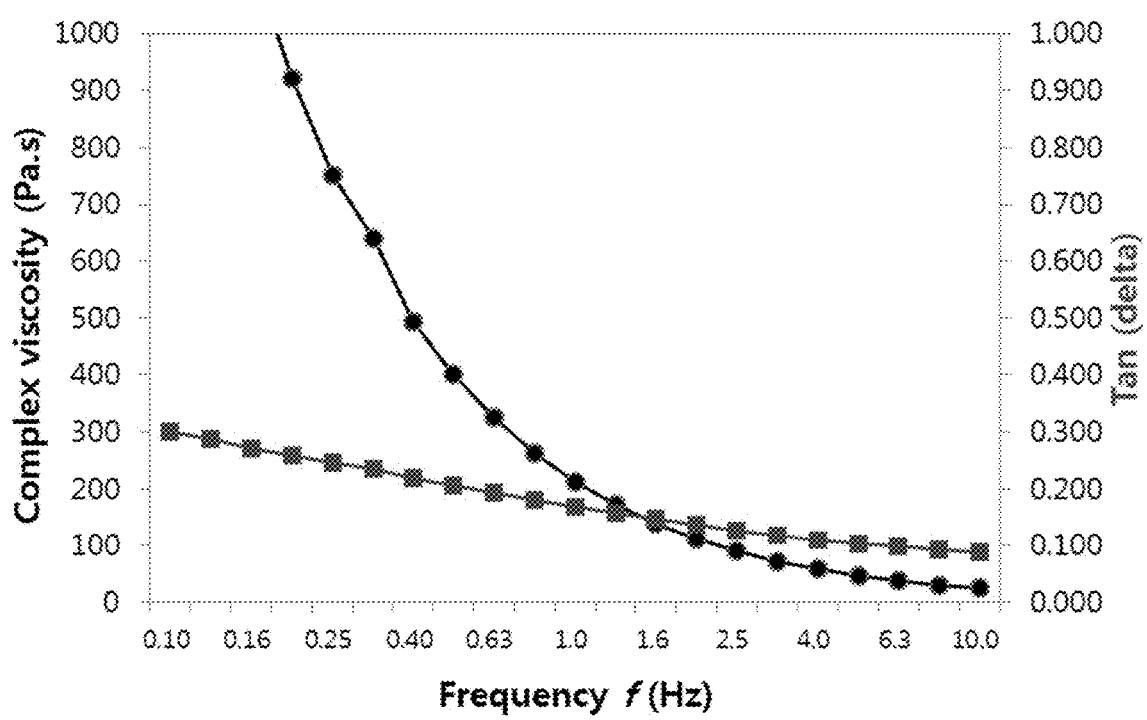

[Fig. 6f]
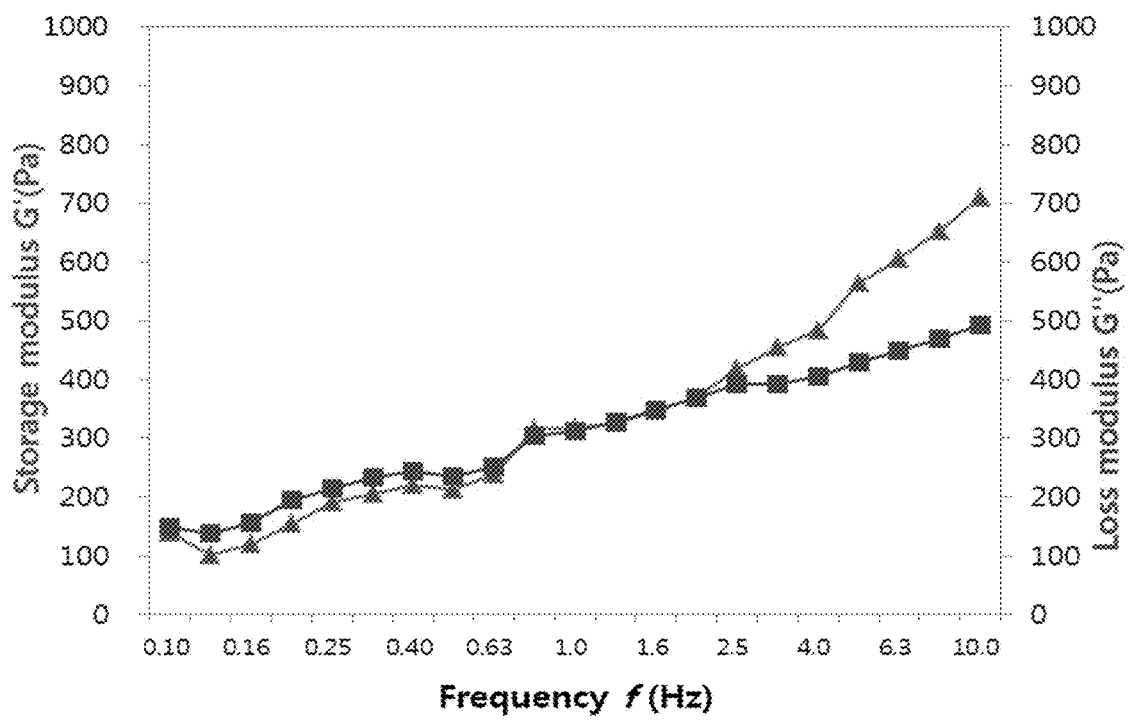
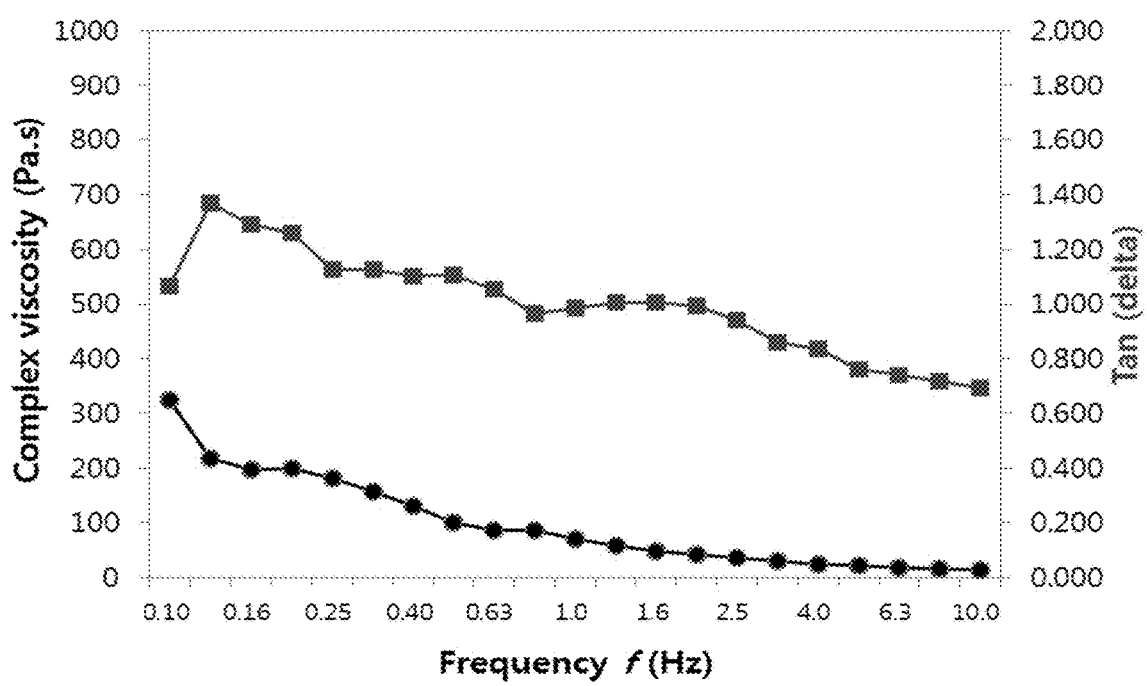

[Fig. 6g]
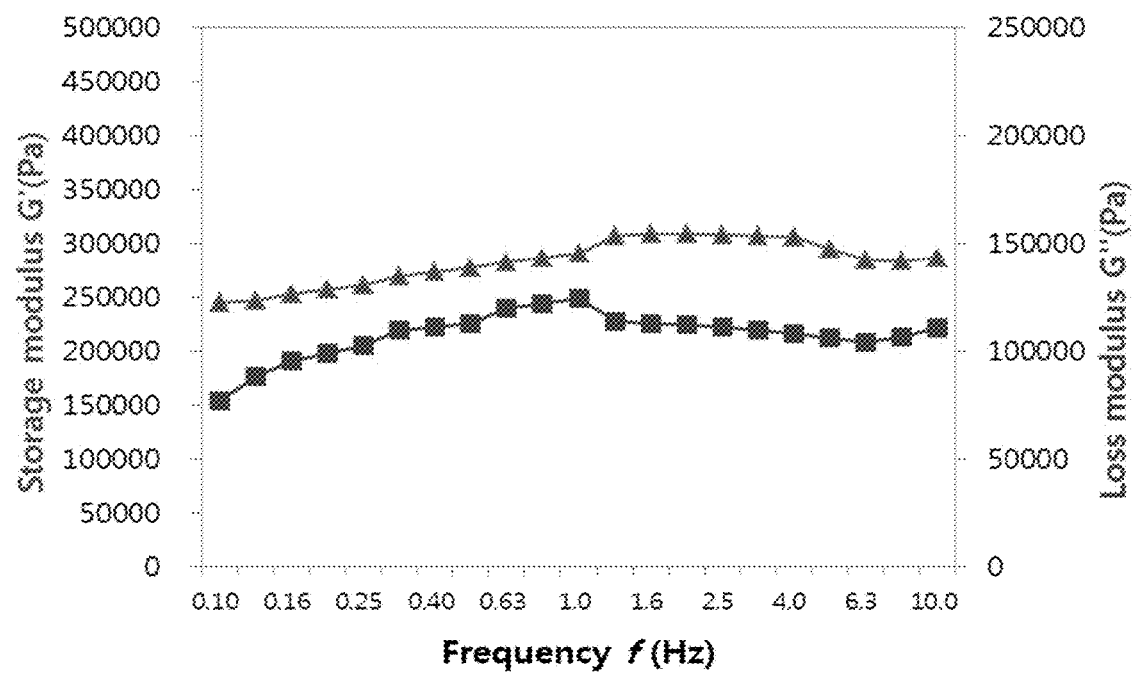
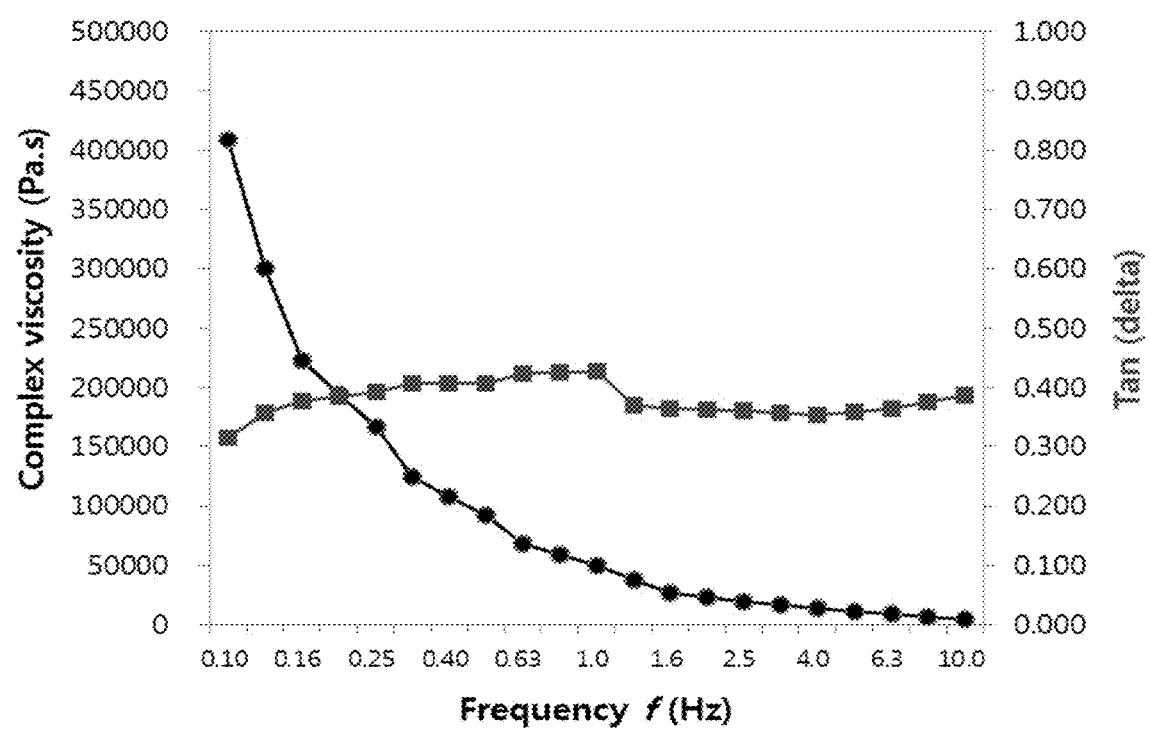

[Fig. 6h]
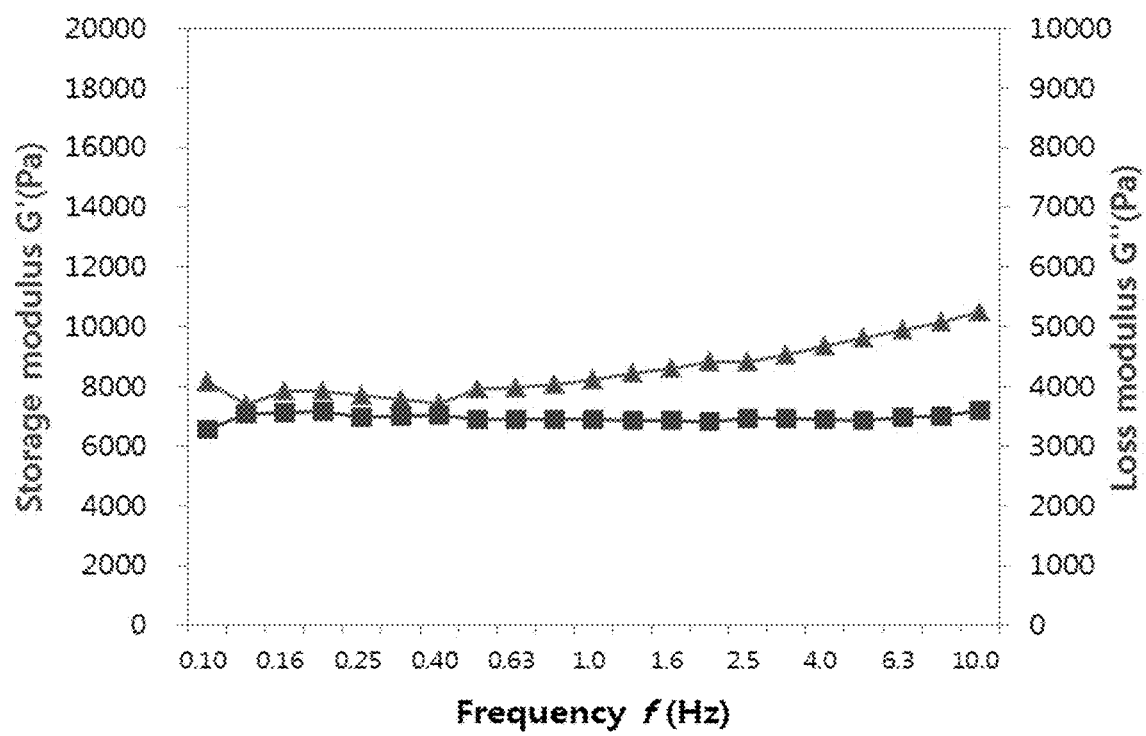
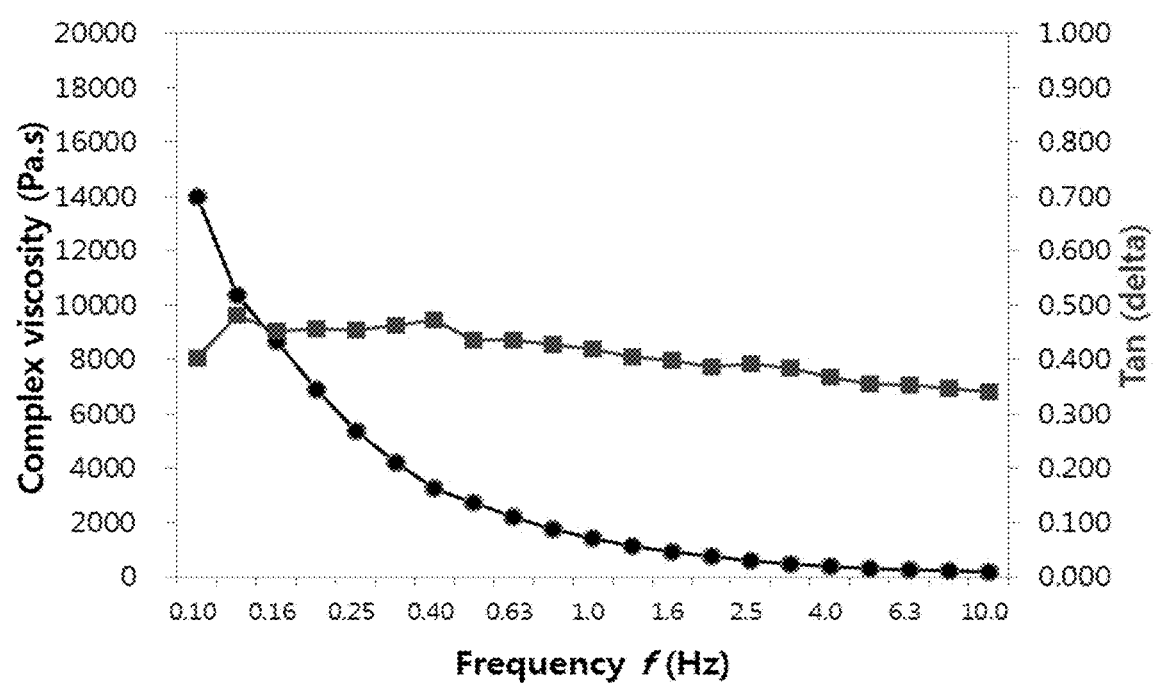

[Fig. 6i]
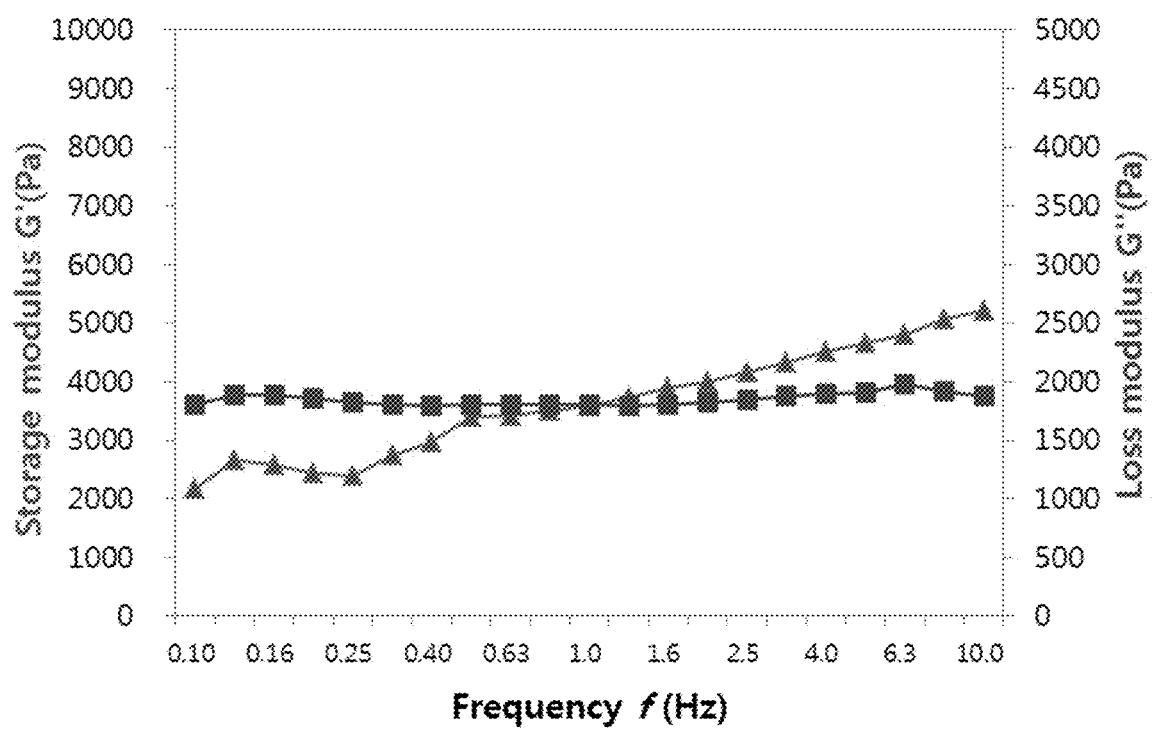
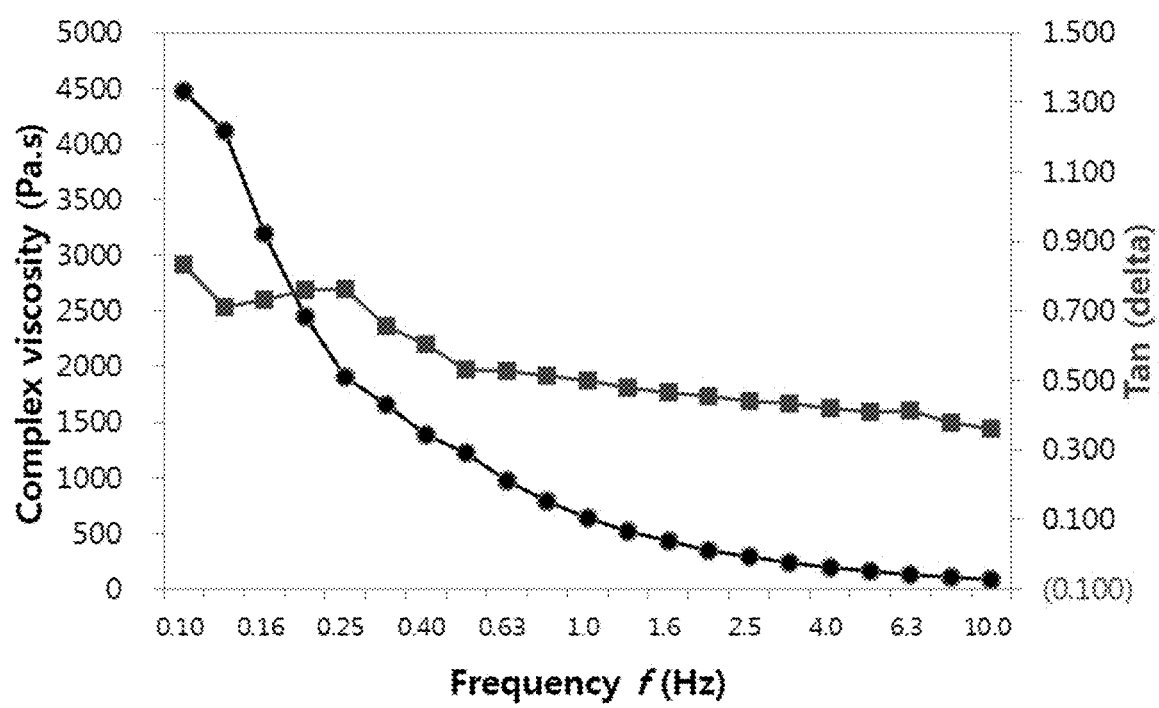

COMPOSITION FOR INJECTION OF HYALURONIC ACID, CONTAINING HYALURONIC ACID DERIVATIVE AND DNA FRACTION, AND USE THEREOF

TECHNICAL FIELD OF THE INVENTION

The present invention relates to an injectable hyaluronic acid composition comprising crosslinked viscoelastic hyaluronic acid derivative and a DNA fraction, for use for cosmetic or therapeutic use. More particularly, the present invention relates to an injectable hyaluronic acid composition comprising a hyaluronic acid derivative with a specific range of degree of crosslinking and a DNA fraction.

BACKGROUND OF THE INVENTION

Hyaluronic acid-based gels for injection have been used for many years for cosmetic purposes, filling or replacement of biological tissues (such as wrinkle filling, remodeling of the face, increasing lip volume, etc.), and the treatment of skin rehydrating by mesotherapy.

In this regard, much effort to improve the physicochemical stability of hyaluronic acid-based gels has been made in order to increase in vivo duration of the gel (i.e. residence time of gel at the injection site) and thereby increase the duration of therapeutic efficacy.

In general, DNA fractions are composed of biopolymers such as phosphates, four (4) kinds of bases, and deoxyriboses. The composition containing these components is an essential component of the cells and is used for various purposes such as medicines for treating and improving wound areas by injecting these fractions into wound areas or the like, and cosmetics for improving wrinkles associated with cell activity.

DNA injection refers to injections containing biomaterials such as polynucleotide (PN) or polydeoxyribonucleotide (PDRN). DNA fractions improves the function of skin by stimulating formation of extracellular matrix (ECM) which is intercellular component, by activating the skin healing ability in the human body thereby recovering the aged and atrophied regenerability of the skin.

Although various filler products have been developed, it is known that there is no functional hyaluronic acid-DNA composite filler product with skin regeneration effect so far.

In addition, in conventional hyaluronic acid filler products, hyaluronic acid derivatives are mixed with non-crosslinked hyaluronic acid to prepare a good feeling during the operation. There is a disadvantage, however, the non-crosslinked hyaluronic acid is easily degraded by the enzyme reaction.

Under these circumstances, the present inventors have made an intensive effort to develop a functional hyaluronic acid-DNA composite filler product. As a result, the present inventors have made an injectable hyaluronic acid composition having not only improved physical properties (viscoelasticity and extrusion force) but also hyaluronidase resistance, by mixing the DNA fractions in a certain ratio to the crosslinked hyaluronic acid composition by a specific preparation method.

DISCLOSURE

Technical Problems

Accordingly, as a solution to the conventional technical problems, the present invention object to provide an injectable hyaluronic acid composition having excellent viscoelasticity and extrusion force by mixing DNA fractions with crosslinked hyaluronic acid and having enzyme resistance, and a manufacturing method thereof.

Effects of the Invention

According to the injectable hyaluronic acid composition and a manufacturing method thereof in the present invention, injectable hyaluronic acid composition with excellent elastic properties and the extrusion force and having enzyme resistance is provided and it can be used helpfully for cosmetic or therapeutic purposes.

BRIEF DESCRIPTION OF THE DRAWINGS

FIGS. 1a to 1i show the results of the storage elastic modulus (G'), loss elastic modulus (G"), Tan (delta), complex viscosity (G) of Examples 1 to 5 and Comparative Examples 1 to 4 for each frequency using a rheometer. Each figures are the result of followings respectively; FIG. 1a: Comparative Example 1, FIG. 1b: Comparative Example 2, FIG. 1c: Comparative Example 3, FIG. 1d: Comparative Example 4, FIG. 1e: Example 1, FIG. 1f: Example 2, FIG. 1g: Example 3, FIG. 1h: Example 4, FIG. 1i: Example 5.

FIGS. 2a and 2b are graphs representing discharge load test results for confirming the extrusion force in a prefilled syringe of the hyaluronic acid main composition according to the present invention.

FIG. 3 shows the electrophoresis result for a PDRN fraction in the injectable hyaluronic acid composition according to the present invention.

FIGS. 4a to 4d represents the graphs of particle size analysis of the crosslinked hyaluronic acid by mixing DNA fractions.

FIG. 5 shows the changes in the viscosity of the hyaluronic acid due to degradation of the hyaluronic acid by hyaluronidase in time.

FIGS. 6a to 6i are graphs comparing rheological properties of Examples and Comparative Examples using rheometer. Each figures are the result of followings respectively; FIG. 6a: Example 7, FIG. 6b: Example 8, FIG. 6c: Example 9, FIG. 6d: Example 10, FIG. 6e: Example 11, FIG. 6f: Example 12, FIG. 6g: Example 13, FIG. 6h: Example 14, FIG. 6i: Example 15.

BEST MODE FOR CARRYING OUT THE INVENTION

In one embodiment of the present invention to accomplish the objects, the present invention refers to an injectable hyaluronic acid composition comprising hyaluronic acid derivatives having a degree of crosslinking of from 0.1 to 200% and the DNA fractions from 0.1 to 50 wt % of the total composition.

The term "hyaluronic acid", as used herein, means a biopolymer material which is repeating units composed with N-acetyl-D-glucosamine and D-glucuronic acid are linearly linked. In the present invention, hyaluronic acid is used to include hyaluronic acid itself, a salt thereof, or a combination thereof. Examples of the salt of hyaluronic acid include, but not limited to, inorganic salts such as sodium hyaluronate, potassium hyaluronate, calcium hyaluronate, magnesium hyaluronate, zinc hyaluronate, and cobalt hyaluronate, and organic salts such as tetrabutylammonium hyaluronate. In the present invention, hyaluronic acid itself or salt thereof may be used alone, or a combination of two or more hyaluronic acid or salt thereof may be used. In the present invention, the molecular weight of the hyaluronic acid may be 100,000 to 5,000,000 Da.

In addition, crosslinked hyaluronic acid derivatives can be prepared by crosslinking hyaluronic acid itself or a salt thereof using a crosslinking agent. For the crosslinking, a method of using a crosslinking agent in an aqueous alkaline solution can be used. The aqueous alkaline solution includes, but not limited to, NaOH, KOH, preferably NAOH aqueous solution. The NaOH aqueous solution can be used at a concentration of 0.25 to 5N. The crosslinked hyaluronic acid derivatives may be a viscoelastic crosslinked hyaluronic acid having Tan δ of 0.01 to 2.0 in the frequency of 0.02 to 1 Hz and complex viscosity of 10 Pa·s (1 Hz) in 25° C.

The crosslinking agent may be a compound containing two or more epoxy functional groups. Preferred examples thereof include 1,4-butandiol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylpropane polyglycidyl ether, 1,2-(bis(2,3-epoxypropoxy)ethylene, pentaerythritol polyglycidyl ether, and sorbitol polyglycidyl ether. 1,4-Butandiol glycidyl ether is particularly preferred.

The term "degree of crosslinking", as used herein, is defined wt % of cross-linking agent to hyaluronic acid monomer units in the crosslinked portion of the hyaluronic acid-based composition. The degree of crosslinking is measured as a weight ratio of the crosslinking agent to the weight ratio of the hyaluronic acid monomer. In the present invention, the degree of crosslinking of the hyaluronic acid is preferably in the range of 0.1 to 200%, and more preferably in the range of 1 to 50% by crosslinking with the crosslinking agent.

Furthermore, the injecting composition according to the present invention includes the hyaluronic acid derivatives representing the certain degree of crosslinking and DNA fractions. In the present invention, the DNA fractions may be selected from, for example, but are not limited to, polynucleotide (PN), or polydeoxyribonucleotide (PDRN). In a preferred embodiment, the concentration of the DNA fractions is 0.01 to 20 mg/ml relative to the total volume of the composition, and is preferably contained in the composition for injection in a proportion of 0.1 to 50 wt % with respect to the total composition, more preferably contained 5 to 30 wt %. In addition, the mixing ratio of the corsslinked hyaluronic acid derivatives and the DNA fractions in the present invention is preferably crosslinked hyaluronic acid derivatives:DNA fractions=from 5.0 to 9.99:from 0.01 to 5.0, more preferably from 7.0 to 9.5:from 0.5 to 3.0 in weight ratio.

Furthermore, in another embodiment, the present invention refers to a manufacturing method of the injectable hyaluronic acid composition. The manufacturing method of injecting composition comprises following steps:

a) preparing the hyaluronic acid derivatives by crosslinking a hyaluronic acid or a salt thereof to a degree of crosslinking of 0.1 to 200% in an aqueous alkali solution using crosslinking agents; and b) mixing the DNA fractions to the hyaluronic acid derivatives having degree of crosslinking of 0.1 to 200% which is prepared in the step a).

Preparation of hyaluronic acid derivatives in the step a) is preferably carried out, by adding a hyaluronic acid or a salt thereof of 1 to 25 wt % based on the aqueous NaOH solution to basic aqueous solution of 0.25 to 5N, and by mixing homogeneously the crosslinking agents having the degree of crosslinking of 0.1 to 200%, preferably 1 to 50%, based on the repeat unit of hyaluronic acid or a salt thereof, with hyaluronic acid and a salt thereof. In one embodiment, the crosslinking reaction with hyaluronic acid and the crosslinking agent in the step may be carried out at 10 to 60° C., more preferably 20 to 50° C., most preferably 25 to 40° C.

In one preferred embodiment, the crosslinked hyaluronic acid derivatives may be further subjected to a process of crushing, washing and swelling with a washing solution, and then pulverizing. The washing solution may be appropriately selected, but saline is preferred.

The basic aqueous solution can be, but are not limited to, KOH or NaOH, preferably NaOH, and is most preferably aqueous solution of NaOH of 0.1 to 5N, particularly 0.25 to 2.5N. In addition, the crosslinking agent can be, but are not limited to, 1,4-butandiol diglycidyl ether (BDDE), ethylene glycol diglycidyl ether (EGDGE), 1,6-hexanediol diglycidyl ether, propylene glycol diglycidyl ether and polypropylene glycol diglycidyl ether.

Furthermore, the injectable hyaluronic acid composition according to the present invention is prepared in step b) by mixing hyaluronic acid derivatives obtained from step a) with DNA fractions. The DNA fractions in this step are the same as the DNA fractions in the injecting composition, and preferably can be carried out by mixing the fraction having a concentration of 0.01 to 20 mg/ml with the DNA fractions obtained from step a). Preferably, the crosslinked hyaluronic acid derivatives obtained from step a) and DNA fractions can be mixed with the following weight ratio: crosslinked hyaluronic acid derivatives:the DNA fractions=5.0 to 9.99: 0.01 to 5.0, preferably, 7.0 to 9.5:0.5 to 3.0.

In an additional embodiment, a step of packing the product in the desired container (e.g. container for prefilled syringe) in order to prepare the final product, and a step of sterilizing packed product after packing can be comprised after the step b) in the manufacturing method.

The injectable hyaluronic acid composition yielded by the manufacturing method by the present invention expresses excellent elastic properties and extrusion force, and have enzyme resistance (particularly, hyaluronidase resistance). In one specific embodiment, the hyaluronic acid composition of the present invention has excellent elastic properties which has much lower Tan(delta) value in the frequency range of 1 Hz than other hyaluronic acid derivatives and hyaluronic acid injections available commercially, by comprise the hyaluronic acid derivatives having certain degree of crosslinking and the DNA fractions (Example 2, FIG. 1f), and represents longer duration of tissue repair due to high resistance to enzyme (Example 2, FIG. 5).

Thus, the hyaluronic acid composition of the present invention can be used for cosmetic or therapeutic purposes due to its characteristic elastic properties, extrusion force, and enzyme resistance. As a specific example, such an injectable hyaluronic acid composition can be used for composition for filling or substitution of biological tissue, filling wrinkle, remodeling of the face, a composition for increase lip volume, a composition for skin rehydration therapy by mesotherapy, a composition for the replacement or temporary replenishment of synovial fluid in arthritis, a composition for increase the volume of sphincter or urethra in the urology or gynecology, a composition for adjuvant or treatment in cataract surgery in ophthalmology, a pharmaceutical gel for release the active substance, or a composition for bone reconstruction, increase in vocal cord volume surgical tissue formation.

Therefore, in another embodiment, the present invention relates to the composition for viscous supplement comprising the injectable hyaluronic acid composition. The composition for viscous supplement can be used for supplementing biological tissue, replacing synovial fluid in arthritis, assisting cataract surgery, or treating glaucoma.

In another embodiment, the present invention relates to the filler for skin injection, composition for treating dry eye syndrome, comprising the injectable hyaluronic acid composition.

MODE FOR INVENTION

Hereinafter, the present invention will be described in more detail through Examples. However, these examples are intended to illustrate the present invention and the scope of the present invention is not limited to these Examples.

Examples 1-4: Preparation of the Hyaluronic Acid-Based Co-Injectable Composition with and without DNA Fractions Example 1

1 g of hyaluronic acid (molecular weight: about 2 million to 3 million Da) was dissolved in 0.25N NaOH solution to 10 wt %. 1,4-Butanediol diglycidyl ether (BDDE) was used by the crosslinking agent, and a definition of the degree of crosslinking used is as follows: weight (BDDE)/weight (dry NaHA).

BDDE was added in amount of 5% of degree of crosslinking and mixed. The gel obtained by the crosslinking reaction of the mixed solution in the constant temperature water bath was crushed in a certain size, and washed and swelled with buffer solution. Hyaluronic acid derivatives were obtained after pulverizing swelled gel using pulverizer. The prepared gels were packed in glass bottles with 200 mL each, and sterilized by heating.

Example 2

Hyaluronic acid (molecular weight: about 2 million to 3 million Da) was mixed with NaOH solution of 0.25N, to 10 wt %, and 1,4-butanediol diglycidyl ether was added with amount of degree of crosslinking of 5%, and crosslinked in the constant temperature water bath. The hyaluronic acid-based PDRN complex gel containing 1.875 mg/ml of PRDN was prepared by adding PDRN fractions (12.5 mg/mL) dissolved in physiological saline solution of 15 wt % to the crosslinked gel.

Example 3

Hyaluronic acid (molecular weight: about 2 million to 3 million Da) was dissolved in 1.25N NaOH solution to 10 wt %, and 1,4-butanediol diglycidyl ether was added with amount of degree of crosslinking of 5%, and crosslinked in the constant temperature water bath. The hyaluronic acid-based PDRN complex gel containing 1.875 mg/ml PRDN was prepared by adding PDRN fractions (12.5 mg/mL) dissolved in physiological saline solution of 15 wt % to the crosslinked gel.

Example 4

Hyaluronic acid (molecular weight: about 2 million to 3 million Da) was dissolved in 2.5N NaOH solution to 10 wt %, and 1,4-butanediol diglycidyl ether was added with amount of degree of crosslinking of 5%, and crosslinked in the constant temperature water bath. The hyaluronic acid-based PDRN complex gel containing 1.875 mg/ml PRDN was prepared by adding PDRN fractions (12.5 mg/mL) dissolved in physiological saline solution of 15 wt % to the crosslinked gel.

Example 5

The gel was prepared by adding 20 mg/mL of HA (molecular weight: 0.8 million to 1 million Da) to the gel prepared with the method of Example 2, to 15 wt %.

Experimental Example 1: Investigation of Viscoelastic Property of the Injectable Hyaluronic Acid Composition (Gel) Prepared by the Present Invention The rheological properties of the prepared Example 1 to 4 and Comparative Example 1 to 3, were analyzed done by using rheometer (Comparative Example 1: LG IVOIRE, Comparative Example 2: BNC Cutegel, Comparative Example 3: GALDERMA Restylane, Comparative Example 4: Humedix elravie).

Analysis Conditions of the Rotational Rheometer (1) Instrument: Rotational Rheometer (KINEXUS pro+)
(2) Frequency: 0.1~10 Hz
(3) Temperature: 25° C.
(4) Strain: 5%
(5) Measuring geometry: 20 mm plate
(6) Measuring gap: 0.5 mm The result values of storage elastic modulus (G'), loss elastic modulus (G"), Tan (delta), complex viscosity (G) depending on frequency with the condition above are shown in the FIGS. 1a to 1i and Table 1.

TABLE 1

|  | G' (Pa) | G" (Pa) | Tan (delta) | Complex viscosity (Pa · s) |
| --- | --- | --- | --- | --- |
| Example 1 | 366 | 115 | 0.315 | 61 |
| Example 2 according to the present invention | 1,012 | 120 | 0.118 | 162 |
| Example 3 | 458 | 116 | 0.254 | 75 |
| Example 4 | 447 | 136 | 0.304 | 74 |
| Example 5 | 5.6 | 1.5 | 0.260 | 0.9 |
| Comparative Example 1 | 390 | 63 | 0.161 | 63 |
| Comparative Example 2 | 705 | 508 | 0.721 | 138 |
| Comparative Example 3 | 502 | 255 | 0.508 | 90 |
| Comparative Example 4 | 278 | 38 | 0.137 | 45 |

(Comparative Example 1: LG IVOIRE, Comparative Example 2: BNC Cutegel, Comparative Example 3: GALDERMA Restylane, Comparative Example 4: Humedix elravie)

Through the Table 1 and FIGS. 1a to 1i, it is considered that the Example 2 according to the present invention has higher complex viscosity, and more excellent elastic properties (lower Tan delta) than Example 1, 3, and 4, Comparative Examples 1 to 4. In Comparative Examples 1 to 4, the Comparative Examples 2 and 3 show high complex viscosity but lower elastic properties, and Comparative Examples 1 and 4 show good elastic properties but low complex viscosity. Through the result of Comparative Example 2 to 4, as the NaOH concentration increases, the viscoelasticity decreases, it is identified that the hyaluronic acid-based crosslinked gel have the best properties when it is mixed with DNA fractions, after crosslinked under the basic conditions of NaOH under 2.5N.

Experimental Example 2: The Discharge Load Test of the Hyaluronic Acid Gel According to the Present Invention The discharge load test was performed to determine the extrusion force of the prefilled syringe of the hyaluronic acid compositions of Example 1 and Example 2.

Analysis Conditions for a Discharge Load Test (1) Instrument: Universal Testing Machine
(2) Testing velocity: 30 mm/min
(3) Measured displacement: 20 mm
(4) Load cell: 200N
(5) Test environment: (25 ± 2) ° C., (45 ± 5) % RH The results under the analysis conditions above are shown in FIGS. 2a and 2b.

As shown in the FIGS. 2a and 2b, the Example 2 according to the present invention represents lower discharge load result values than the Example 1 comprising only the crosslinked hyaluronic acid derivatives. It is confirmed that mixing of the DNA fractions with the crosslinked hyaluronic acid derivatives show not only excellent elasticity but also increase of softness of the gel which is importantly considered when treat it.

Experimental Example 3: Investigation of PDRN Content of the Hyaluronic Acid Gel Prepared by the Present Invention To investigate the PDRN fraction contained in hyaluronic acid of Example 1 and the injectable hyaluronic acid composition of Example 2 according to the present invention, electrophoresis was performed. FIG. 3 shows the result.

As shown in FIG. 3, the PDRN fractions (c) included in Example 2 according to the present invention represent the same molecular weight as compared with the control PDRN (a) before mixing and Example 1. The result suggests that the hyaluronic acid gel doesn't affect to the molecular weight of the PDRN fractions.

Experimental Example 4: Particle Size Analysis of the Hyaluronic Acid Derivatives by Mixing of DNA Fractions In order to determine the particle size and distribution of the hyaluronic acid composition of Examples 1 to 4 and Comparative Examples 1 to 3, the particles with the size of between 0.375 um to 2000 um are counted after dilute each samples of 3 g with distilled water of 15 mL, by using Beckman Coulter LS Particle Size Analyzer. The results are shown in FIG. 4 and Table 2 (Comparative Example 1: LG IVOIRE, Comparative Example 2: BNC Cutegel).

TABLE 2

| Examples | Average particle size(um) |
|---|---|
| Example 1 | 1064 ± 13 |
| Example 2 | 1072 ± 14 |

TABLE 2-continued

| Examples | Average particle size(um) |
|---|---|
| Comparative Example 1 | 1060 ± 15 |
| Comparative Example 2 | 924 ± 21 |

As shown in Table 2 and FIGS. 4a to 4d, the composition of Example 2 according to the present invention, showed homogeneous particle distribution compared to Comparative Example 1 and 2, and similar average particle size with Example 1. The result confirms that the DNA fraction doesn't affect to particle size of hyaluronic acid.

Experimental Example 5: Enzyme Resistance Analysis of the Hyaluronic Acid Derivatives According to the Present Invention 5 g of hyaluronic acid of Example 2 and Comparative Example 1 (LG life Sciences IVOIRE) and 2.5 g hyaluronidase of 100 IU/mL were put into the conical tubes respectively and mixed homogeneously. Reaction was performed in the 37° C. constant temperature water bath. Changes in viscosity of hyaluronic acid by time were measured using Ubbelohde viscometer. The higher the hyaluronidase resistance is, the less the viscosity rate changes. The higher viscosity rate means less viscosity.

The result is shown in FIG. 5.

As shown in FIG. 5, the composition of Example 2 according to the present invention (HA content: 19.8 mg/ml) shows slow increase of the viscosity rate (the lower slope) under the hyaluronidase treatment (the higher viscosity rate means less viscosity of the solution) than composition of the Comparative Example 1 (HA content: 20.3 mg/ml). Thus, the hyaluronic acid derivatives of the present invention have more excellent enzyme resistance than Comparative Example 1 available commercially.

Examples 6 to 15: Preparation of Hyaluronic Acid-Based Gel According to the Degree of Crosslinking and the Mixing Ratio of the DNA Fractions Example 6

Hyaluronic acid (molecular weight: about 2 million to 3 million Da) was mixed with 0.25N NaOH solution, to 10 wt %, and BDDE in an amount corresponding to have the degree of crosslinking 0.05% was added. As the result of crosslinking, the gel was not formed.

Examples 7 to 9

Hyaluronic acid (molecular weight: about 2 million to 300 million Da) was mixed with 0.25N NaOH solution, to 10 wt %, and BDDE in an amount corresponding to have the degree of crosslinking 0.1% was added to and mixed. The PDRN fractions dissolved in water (80 ml/mL) were added to the crosslinked gel, to of 0.1 wt % (Example 7), of 50 wt % (Example 8), of 70 wt % (Example 9) respectively, and the hyaluronic acid-based PDRN complex gels containing 1.875 mg/mL PDRN were prepared.

Examples 10 to 12

Hyaluronic acid (molecular weight: about 2 million to 300 million Da) was mixed with 0.25N NaOH solution, to 10 wt %, and BDDE in an amount corresponding to have the degree of crosslinking 200% was added to and mixed. The PDRN fractions dissolved in water (80 ml/mL) were added to the crosslinked gel, to of 0.1 wt % (Example 10), of 50 wt % (Example 11), of 70 wt % (Example 12) respectively, and the hyaluronic acid-based PDRN complex gels containing 1.875 mg/mL PDRN were prepared.

Examples 13 to 15

Hyaluronic acid (molecular weight: about 2 million to 300 million Da) was mixed with 0.25N NaOH solution, to 10 wt %, and BDDE in an amount corresponding to have the degree of crosslinking 400% was added to and mixed. The PDRN fractions dissolved in water (80 ml/mL) were added to the crosslinked gel, to of 0.1 wt % (Example 13), of 50 wt % (Example 14), of 70 wt % (Example 15) respectively, and the hyaluronic acid-based PDRN complex gels containing 1.875 mg/mL PDRN were prepared.

Experimental Example 6: Comparison of Properties of Hyaluronic Acid Composition (Gel) of Examples 6 to 14

Rheological properties of prepared Examples 6 to 14 were compared using rheometer. The result values of storage elastic modulus (G'), loss elastic modulus (G"), Tan (delta), complex viscosity (G) depending on frequency are shown in the FIGS. 6a to 6i and Table 3.

TABLE 3

| | Frequency: 1.0 (Hz) | | | |
|---|---|---|---|---|
| | G' (Pa) | G" (Pa) | Tan (delta) | Complex viscosity (Pa · s) |
| Example 7 | 407 | 27 | 0.067 | 65 |
| Example 8 | 507 | 134 | 0.126 | 84 |
| Example 9 | 139 | 18 | 0.126 | 22 |
| Example 10 | 468 | 119 | 0.254 | 77 |
| Example 11 | 506 | 100 | 0.197 | 82 |
| Example 12 | 317 | 312 | 0.985 | 71 |
| Example 13 | 290,760 | 124,537 | 0.428 | 50,342 |
| Example 14 | 8,226 | 3,446 | 0.419 | 1,420 |
| Example 15 | 3,596 | 1,800 | 0.501 | 640 |

As shown in FIGS. 6a to 6i and Table 3, the gels from Example 7, Example 8, Example 10, and Example 11 had both excellent viscoelasticity values and low Tan delta values compared with the other crosslinked gels. Thus, the optimal preparation method for the hyaluronic acid-based gel comprising the DNA fractions was confirmed (using NaOH below 2.5N, BDDE degree of crosslinking 0.1 to 200%, DNA mixing ratio 0.1 to 50 wt %).

The invention claimed is:

1. A method for repair or replacement of biological tissue, filling wrinkle, remodeling of the face or increasing lip volume, skin rehydration by mesotherapy, replacement or supplement of joint synovial fluid or treating dry eye syndrome, comprising administering to the subject an effective amount of an injectable hyaluronic acid composition comprising hyaluronic acid derivatives having the degree of crosslinking of 0.1 to 200% wherein the concentration of the hyaluronic acid derivative is 1 to 50 mg/ml and DNA fractions of 0.1 to 50 wt % based on the total composition.

2. The method of claim 1, wherein the concentration of the DNA fraction is 0.001 to 40 mg/ml.

3. The method of claim 1, wherein the molecular weight of the hyaluronic acid derivatives is 100,000 to 5,000,000 Da.

4. The method of claim 1, wherein the DNA fraction is selected from the group consisting polynucleotide (PN), and polydeoxyribonucleotide (PDRN).

5. The method of claim 1, wherein the weight ratio of the crosslinked hyaluronic acid derivatives:the DNA fractions is 5.0 to 9.99:0.01 to 5.0.

6. A manufacturing method of hyaluronic acid injecting composition comprising:
   a) preparing the hyaluronic acid derivatives by crosslinking hyaluronic acid or a salt thereof in an aqueous alkali solution at a degree of crosslinking of 0.1 to 200% using a crosslinking agent; and
   b) mixing DNA fractions with the hyaluronic acid derivatives having degree of crosslinking of 0.1 to 200%, prepared in step a),
   wherein the hyaluronic acid injecting composition comprising hyaluronic acid derivatives having the degree of crosslinking of 0.1 to 200% wherein the concentration of the hyaluronic acid derivative is 1 to 50 mg/ml and DNA fractions of 0.1 to 50 wt % based on the total composition.

7. The manufacturing method of claim 6, the aqueous alkali solution is aqueous NaOH solution.

8. The manufacturing method of claim 7, wherein the concentration of the aqueous NaOH solution is 0.25 to 2.5N.

9. The manufacturing method of claim 7, wherein the crosslinking agent is 1,4-butanediol diglycidyl ether.

10. The method of claim 1, wherein the injectable hyaluronic acid composition is in form of a skin injectable filler.

11. The method of claim 1, wherein the injectable hyaluronic acid composition is in form of a pharmaceutical-composition.

12. The method of claim 1, wherein the injectable hyaluronic acid composition is in form of a cosmetic composition.

* * * * *